(12) United States Patent
Chen et al.

(10) Patent No.: US 12,020,434 B2
(45) Date of Patent: Jun. 25, 2024

(54) SEGMENTATION AND VIEW GUIDANCE IN ULTRASOUND IMAGING AND ASSOCIATED DEVICES, SYSTEMS, AND METHODS

(71) Applicant: KONINKLIJKE PHILIPS N.V., Eindhoven (NL)

(72) Inventors: Alvin Chen, Cambridge, MA (US); Kunal Vaidya, Boston, MA (US); Brian Lee, Rockville, MD (US); Vipul Shrihan Pai Raikar, Somerville, MA (US); Mingxin Zheng, Cambridge, MA (US); Shyam Bharat, Arlington, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 362 days.

(21) Appl. No.: 17/599,590

(22) PCT Filed: Mar. 30, 2020

(86) PCT No.: PCT/EP2020/058898
§ 371 (c)(1),
(2) Date: Sep. 29, 2021

(87) PCT Pub. No.: WO2020/201183
PCT Pub. Date: Oct. 8, 2020

(65) Prior Publication Data
US 2022/0198669 A1 Jun. 23, 2022

Related U.S. Application Data
(60) Provisional application No. 62/964,715, filed on Jan. 23, 2020, provisional application No. 62/828,185, filed on Apr. 2, 2019.

(51) Int. Cl.
*A61B 34/20* (2016.01)
*A61B 8/00* (2006.01)
(Continued)

(52) U.S. Cl.
CPC .......... *G06T 7/0016* (2013.01); *A61B 8/0841* (2013.01); *A61B 8/461* (2013.01);
(Continued)

(58) Field of Classification Search
CPC . G06T 2207/10132; G06T 2207/20081; G06T 2207/20084; G06T 2207/30048;
(Continued)

(56) References Cited

U.S. PATENT DOCUMENTS 10,426,442 B1 * 10/2019 Schnorr ............... A61B 8/5223
2003/0153823 A1 * 8/2003 Geiser .................. G06T 7/0012
600/407

(Continued)

OTHER PUBLICATIONS

Xin Yang, "Fine-Grained Recurrent Neural Networks for Automatic Prostate Segmentation in Ultrasound Imagess," Feb. 12, 2017, Proceedings of the Thirty-First AAAI Conference on Artificial Intelligence (AAAI-17), pp. 1633-1638.*
Sepehr Valipour, "Recurrent Fully Convolutional Networks for Video Segmentation,"May 15, 2017, 2017 IEEE Winter Conference on Applications of Computer Vision,pp. 29-34.*
Emran Mohammad Abu Anas, "A deep learning approach for real time prostate segmentation infreehand ultrasound guided biopsy," Jun. 1, 2018,Medical Image Analysis 48 (2018),pp. 107-114.*
(Continued)

*Primary Examiner* — Omar S Ismail

(57) ABSTRACT

Ultrasound image devices, systems, and methods are provided. An ultrasound imaging system comprising a processor circuit configured to receive, from an ultrasound imaging device, a sequence of input image frames of a moving object over a time period, wherein the moving object comprises at least one of an anatomy of a patient or a medical device traversing through the patient's anatomy, and wherein a portion of the moving object is at least partially invisible in a first input image frame of the sequence of input image frames; apply a recurrent predictive network to the sequence
(Continued)

of input image frames to generate segmentation data; and output, to a display, a sequence of output image frames based on the segmentation data, wherein the portion of the moving object is fully visible in a first output image frame of the sequence of output image frames.

15 Claims, 14 Drawing Sheets

(51) Int. Cl.
    *A61B 8/08*     (2006.01)
    *G06T 7/00*     (2017.01)
    *G06T 7/11*     (2017.01)
    *G06T 7/20*     (2017.01)
    *G06T 7/70*     (2017.01)

(52) U.S. Cl.
    CPC .............. *A61B 8/483* (2013.01); *A61B 34/20* (2016.02); *G06T 7/11* (2017.01); *G06T 7/20* (2013.01); *G06T 7/70* (2017.01); *A61B 2034/2063* (2016.02); *G06T 2207/10132* (2013.01); *G06T 2207/20081* (2013.01); *G06T 2207/20084* (2013.01); *G06T 2207/30048* (2013.01); *G06T 2207/30101* (2013.01)

(58) Field of Classification Search
    CPC ......... G06T 2207/30101; G06T 7/0016; G06T 7/11; G06T 7/20; G06T 7/70; A61B 2034/2063; A61B 34/20; A61B 8/0841; A61B 8/461; A61B 8/483
    See application file for complete search history.

(56) References Cited

U.S. PATENT DOCUMENTS

| | | | | |
|---|---|---|---|---|
| 2004/0225221 | A1* | 11/2004 | Olsson | A61B 8/5238 600/447 |
| 2006/0030777 | A1* | 2/2006 | Liang | G06T 7/0012 600/437 |
| 2011/0243401 | A1* | 10/2011 | Zabair | G06T 7/33 382/128 |
| 2011/0274326 | A1* | 11/2011 | Allain | G06T 7/12 382/128 |
| 2015/0253428 | A1* | 9/2015 | Holz | G01S 7/483 356/5.01 |
| 2018/0247199 | A1* | 8/2018 | Cox | G06N 3/084 |
| 2019/0163978 | A1* | 5/2019 | Yang | G06F 18/217 |
| 2020/0090345 | A1* | 3/2020 | Krebs | A61B 5/7267 |

OTHER PUBLICATIONS

Arash Pourtaherian, "Robust and semantic needle detection in 3D ultrasound using orthogonal-plane convolutional neural networks," May 31, 2018, International Journal of Computer Assisted Radiology and Surgery (2018) 13,pp. 1321-1330.*
Olaf Ronneberger, "U-Net: Convolutional Networks for Biomedical Image Segmentation,"Nov. 18, 2015, Lecture Notes in Computer Science book series (LNIP, vol. 9351), Part III, LNCS 9351,pp. 234-239.*
Kristen M. Meiburger, "Automated localization and segmentation techniques for B-mode ultrasound images: A review,"Nov. 30, 2017,Computers in Biology and Medicine 92 (2018),pp. 210-228.*
Alireza Mehrtash, "Automatic Needle Segmentation and Localization in MRI With 3-D Convolutional Neural Networks: Application to MRI-Targeted Prostate Biopsy,"Oct. 18, 2018,IEEE Transactions On Medical Imaging, vol. 38, No. 4, Apr. 2019,pp. 1026-1033.*
Bishesh Khanal, "EchoFusion: Tracking and Reconstruction of Objects in 4D Freehand Ultrasound Imaging Without External Trackers,"Sep. 15, 2018,Lecture Notes in Computer Science book series (LNIP,vol. 11076),pp. 117-125.*
Xin Yang ,"Towards Automated Semantic Segmentation in Prenatal Volumetric Ultrasound,"Jul. 23, 2018, IEEE Transactions On Medical Imaging, vol. 38, No. 1, Jan. 2019,pp. 180-189.*
Chen et al: "Combining Fully Convolutional and Recurrent Neural Networks for 3D Biomedical Image Segmentation"; 30th Conference On Nerual Information Processing Systems (NIPS 2016), Barcelona, Spain, pp. 3044-3052.
PCT/EP2020/058898, ISR & WO, Jul. 9, 2020.
Khanal et al: "Echofusion: Tracking and Reconstruction of Objects in 4D Freehand Ultrasound Imaging Without External Trackers"; LNCS 11076, pp. 117-127, 2018.
Milletari et al: "V-Net:Fully Convolutional Neural Networks for Volumetric Medical Image Segmentation";ARxIV:1606.04797V1, Jun. 15, 2016, 11 Page Document.
Pourtaherian et al: "Robust and Semantic Needle Detection in 3D Ultrasound Using Orthogonal-Plane Convolutional Neural Networks"; International Journal of Computer Assisted Radiology and Surgery, 2018.
Ronneberger et al: "U-Net:Convolutional Networks for Biomedical Image Segmentation", Med. Image Comput. Comput. Interv., 9351, 565-571, 2016.
Valipour et al: "Recurrent Fully Convolutional Networks for Video Segmentation", Proc. 2017 IEEE Winter Conf. Appl. Comput Vis. 2017.
Yang et al: "Fine-Grained Recurrent Neural Networks for Automatic Prostate Segmentation in Ultrasound Images"; 2017, Association for the Advancement of Artifical Intelligence, 8 Page Document.

* cited by examiner

SEGMENTATION AND VIEW GUIDANCE IN ULTRASOUND IMAGING AND ASSOCIATED DEVICES, SYSTEMS, AND METHODS

CROSS-REFERENCE TO PRIOR APPLICATIONS

This application is the U.S. National Phase application under 35 U.S.C. §371 of International Application No. PCT/EP2020/058898, filed on Mar. 30, 2020, which claims the benefit of U.S. Provisional Patent Application No. 62/964,715, filed on Jan. 23, 2020 and U.S. Provisional Patent Application No. 62/828,185, filed on Apr. 2, 2019. These applications are hereby incorporated by reference herein.

TECHNICAL FIELD

The present disclosure relates generally to ultrasound imaging and, in particular, to providing segmentation of moving objects and guidance for locating an optimal imaging view.

BACKGROUND

Ultrasound can provide non-radiated, safe, and real-time, dynamic imaging of anatomy and/or medical devices during medical procedures (e.g., diagnostics, interventions, and/or treatments). Traditionally, clinicians have relied on two-dimensional (2D) ultrasound imaging to provide guidance in diagnostic and/or navigations of medical devices through a patient's body during medical procedures. However, in some cases, medical devices and/or anatomical structures can be thin, non-rigid, and/or moving, making them difficult to identify in 2D ultrasound images. Similarly, anatomical structures may be thin, tortuous, and in some cases, may be in constant motion (e.g. due to breathing, cardiac, and/or arterial pulses).

The recent development and availability of three-dimensional (3D) ultrasound enable viewing of 3D volumes instead of 2D image slices. The ability to visualize 3D volumes can be valuable in medical procedures. For instance, the tip of a medical device may be uncertain in a 2D image slice due to foreshortening, but may be clear when viewing in a 3D volume. Operations such as the positioning of an optimal imaging plane in a 3D volume can benefit significantly with four-dimensional (4D) imaging (e.g., 3D imaging across time). Examples of clinical areas that can benefit from 3D and/or 4D imaging may include diagnostics and/or treatments of peripheral vascular disease (PVD) and structural heart disease (SHD).

While 3D and/or 4D imaging can provide valuable visualization and/or guidance to medical procedures, the interpretation of 3D and/or 4D imaging data can be complex and challenging due to the high volume, the high dimensionality, the low resolution, and/or the low framerate of the data. For example, accurate interpretations of 3D and/or 4D imaging data may require a user or a clinician with extensive training and great expertise. Additionally, the interpretations of the data can be user dependent. Typically, during an ultrasound-guided procedure, a clinician may spend a large portion of the time in finding an ideal imaging view of the patient's anatomy and/or the medical device.

Computers are generally more proficient in interpreting high-volume, high-dimensionality data. For example, algorithmic models can be applied to assist interpretations of 3D and/or 4D imaging data and/or locating an optimal imaging view. However, traditional algorithms may not perform well in identifying and/or segmenting thin objects and/or moving objects in ultrasound images, for example, due to low signal-to-noise ratio (SNR), ultrasound artefacts, occlusion of devices lying in confusing poses such as along vessel walls, and/or high-intensity artefacts which may resemble the moving object.

SUMMARY

There remains a clinical need for improved systems and techniques for image segmentation and imaging guidance. Embodiments of the present disclosure provide a deep learning network that utilizes temporal continuity information in three-dimensional (3D) ultrasound data and/or four-dimensional (4D) ultrasound data to segment a moving object and/or provide imaging guidance. 3D ultrasound data may refer to a time series of 2D images obtained from 2D ultrasound imaging across time. 4D ultrasound data may refer to a time series of 3D volumes obtained from 3D ultrasound imaging across time. The temporally-aware deep learning network includes a recurrent component (e.g., a recurrent neural network (RNN)) coupled to a plurality of convolutional encoding-decoding layers operating at multiple different spatial resolutions. The deep learning network is applied to a time series of 2D or 3D ultrasound imaging frames including a moving object and/or a medical device. The recurrent component passes the deep learning network's prediction for a current image frame as a secondary input to a prediction of a next image frame.

In an embodiment, the deep learning network is trained to differentiate a flexible, elongate, thinly-shaped medical device (e.g., a catheter, a guide wire, a needle, a therapy device, and/or a treatment device) passing through an anatomical structure (e.g., heart, lungs, and/or vessels) from the anatomical structure and predict a position and/or motion of the medical device based on time-continuity information in the ultrasound image frames. In an embodiment, the deep learning network is trained to identify a moving portion of an anatomical structure caused by cardiac motion, breathing motion, and/or arterial pulses from a static portion of the anatomical structure and predict motion of the moving portion based on time-continuity information in the ultrasound image frames. In an embodiment, the deep learning network is trained to predict a target imaging plane of an anatomical structure. The deep learning network's prediction can be used to generate a control signal and/or an instruction (e.g., rotation and/or translation) to automatically steer ultrasound beams for imaging the target imaging plane. Alternatively, the deep learning network's prediction can be used to provide a user with instructions for navigating an ultrasound imaging device towards the target imaging plane. The deep learning network can be applied in real-time during 3D and/or 4D imaging to provide dynamic segmentations and imaging guidance.

In one embodiment, an ultrasound imaging system comprising a processor circuit in communication with an ultrasound imaging device, the processor circuit configured to receive, from the ultrasound imaging device, a sequence of input image frames of a moving object over a time period, wherein the moving object comprises at least one of an anatomy of a patient or a medical device traversing through the patient's anatomy, and wherein a portion of the moving object is at least partially invisible in a first input image frame of the sequence of input image frames; apply a recurrent predictive network associated with image segmentation to the sequence of input image frames to generate segmentation data; and output, to a display in communication with the processor circuit, a sequence of output image frames based on the segmentation data, wherein the portion of the moving object is fully visible in a first output image frame of the sequence of output image frames, the first output image frame and the first input image frame associated with a same time instant within the time period.

In some embodiments, wherein the processor circuit configured to apply the recurrent predictive network is further configured to generate previous segmentation data based on a previous input image frame of the sequence of input image frames, the previous input image frame being received before the first input image frame; and generate first segmentation data based on the first input image frame and the previous segmentation data. In some embodiments, wherein the processor circuit configured to generate the previous segmentation data is configured to apply a convolutional encoder and a recurrent neural network to the previous input image frame; the processor circuit configured to generate the first segmentation data is configured to apply the convolutional encoder to the first input image frame to generate encoded data; and apply the recurrent neural network to the encoded data and the previous segmentation data; and the processor circuit configured to apply the recurrent predictive network is further configured to apply a convolutional decoder to the first segmentation data and the previous segmentation data. In some embodiments, wherein the convolutional encoder, the recurrent neural network, and the convolutional decoder operate at multiple spatial resolutions. In some embodiments, wherein the moving object includes the medical device traversing through the patient's anatomy, and wherein the convolutional encoder, the recurrent neural network, and the convolutional decoder are trained to identify the medical device from the patient's anatomy and predict a motion associated with the medical device traversing through the patient's anatomy. In some embodiments, wherein the moving object includes the patient's anatomy with at least one of a cardiac motion, a breathing motion, or an arterial pulse, and wherein the convolutional encoder, the recurrent neural network, and the convolutional decoder are trained to identify a moving portion of the patient's anatomy from a static portion of the patient's anatomy and predict a motion associated with the moving portion. In some embodiments, wherein the moving object includes the medical device traversing through the patient's anatomy, and wherein the system comprises the medical device. In some embodiments, wherein the medical device comprises at least one of a needle, a guidewire, a catheter, a guided catheter, a therapy device, or an interventional device. In some embodiments, wherein the input image frames include at least one of two-dimensional image frames or three-dimensional image frames. In some embodiments, wherein the processor circuit is further configured to apply spline fitting to the sequence of input image frames based on the segmentation data. In some embodiments, the system further comprises the ultrasound imaging device, and wherein the ultrasound imaging device comprises an ultrasound transducer array configured to obtain the sequence of input image frames.

In one embodiment, an ultrasound imaging system comprising a processor circuit in communication with an ultrasound imaging device, the processor circuit configured to receive, from the ultrasound imaging device, a sequence of image frames representative of an anatomy of a patient over a time period; apply a recurrent predictive network associated with image acquisition to the sequence of image frames to generate imaging plane data associated with a clinical property of the patient's anatomy; and output, to a display in communication with the processor circuit based on the imaging plane data, at least one of a target imaging plane of the patient's anatomy or an instruction for repositioning the ultrasound imaging device towards the target imaging plane.

In some embodiments, wherein the processor circuit configured to apply the recurrent predictive network is further configured to generate first imaging plane data based on a first image frame of the sequence of image frames; and generate second imaging plane data based on a second image frame of the sequence of image frames and the first imaging plane data, the second image frame being received after the first image frame. In some embodiments, wherein the processor circuit configured to generate the first imaging plane data is configured to apply a convolutional encoder and a recurrent neural network to the first image frame; the processor circuit configured to generate the second imaging plane data is configured to apply the convolutional encoder to the first image frame to generate encoded data; and apply the recurrent neural network to the encoded data and the first imaging plane data; and the processor circuit configured to apply the recurrent predictive network is further configured to apply a convolutional decoder to the first imaging plane data and the second imaging plane data. In some embodiments, wherein the convolutional encoder, the recurrent neural network, and the convolutional decoder operate at multiple spatial resolutions, and wherein the convolutional encoder, the recurrent neural network, and the convolutional decoder are trained to predict the target imaging plane for imaging the clinical property of the patient's anatomy. In some embodiments, wherein the image frames include at least one of two-dimensional image frames or three-dimensional image frames of the patient's anatomy. In some embodiments, wherein the processor circuit is configured to output the target imaging plane including at least one of a cross-sectional image slice, an orthogonal image slice, or a multiplanar reconstruction (MPR) image slice of the patient's anatomy including the clinical property. In some embodiments, the system further comprises the ultrasound imaging device, and wherein the ultrasound imaging device comprises an ultrasound transducer array configured to obtain the sequence of image frames. In some embodiments, wherein the processor circuit is further configured to generate an ultrasound beam steering control signal based on the imaging plane data; and output, to the ultrasound imaging device, the ultrasound beam steering control signal. In some embodiments, wherein the processor circuit is configured to output the instruction including at least one of a rotation or a translation of the ultrasound imaging device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
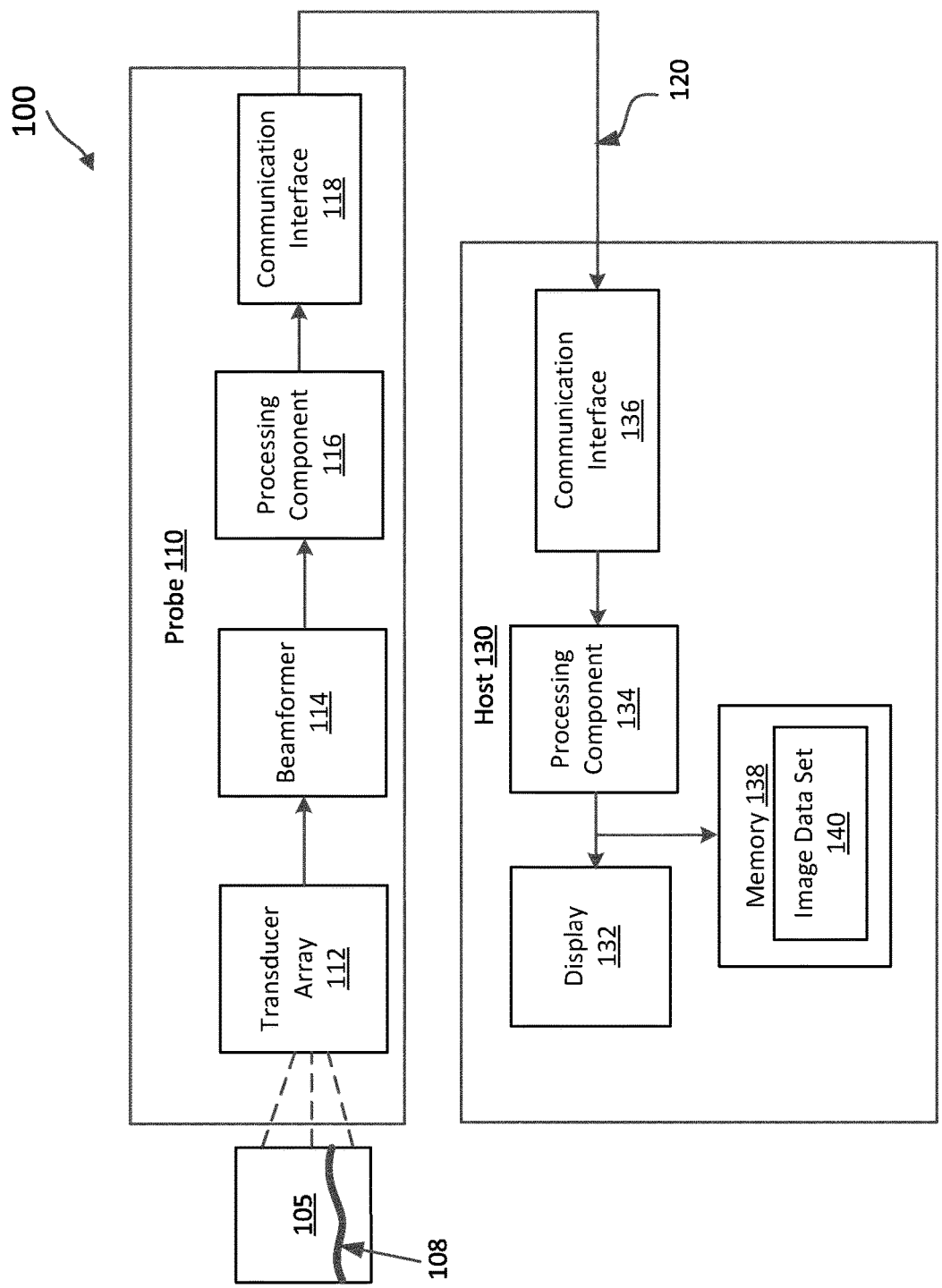
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, and a communication interface 118. The host 130 includes a display 132, a processing component 134, and a communication interface 136.

In an exemplary embodiment, the probe 110 is an external ultrasound imaging device including a housing configured for handheld operation by a user. The transducer array 112 can be configured to obtain ultrasound data while the user grasps the housing of the probe 110 such that the transducer array 112 is positioned adjacent to and/or in contact with a patient's skin. The probe 110 is configured to obtain ultrasound data of anatomy within the patient's body while the probe 110 is positioned outside of the patient's body. In some embodiments, the probe 110 is a transthoracic (TTE) probe. In some other embodiments, the probe 110 can be a trans-esophageal (TEE) ultrasound probe.

The transducer array 112 emits ultrasound signals towards an anatomical object 105 of a patient and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy, such as blood vessels, nerve fibers, airways, mitral leaflets, kidney, and/or liver of a patient that is suitable for ultrasound imaging examination. In some embodiments, the object 105 may include at least a portion of a patient's heart, lungs, and/or skin. In some embodiments, the object 105 may be in constant motion, for example, resulted from breathing, cardiac activities, and/or arterial pulses. The motion may be regular or periodic, for example, with motion of the heart, associated vessels, and/or lungs in the context of a cardiac cycle or a heartbeat cycle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

In some embodiments, the system 100 is used to guide a clinician during a medical procedure (e.g., treatment, diagnostic, therapy, and/or interventions). For example, the clinician may insert a medical device 108 into the anatomical object 105. In some examples, the medical device 108 may include an elongate flexible member with a thin geometry. In some examples, the medical device 108 may be a guide wire, a catheter, a guide catheter, a needle, an intravascular ultrasound (IVUS) device, a diagnostic device, a treatment/therapy device, an interventional device, and/or intracatheter imaging device. In some examples, the medical device 108 may be any imaging device suitable for imaging a patient's anatomy and may be of any suitable imaging modalities, such as optical tomography (OCT), and/or endoscopy. In some examples, the medical device 108 may include a sheath, an imaging device, and/or an implanted device. In some examples, the medical device 108 may be a treatment/therapy device including a balloon, a stent, and/or an atherectomy device. In some examples, the medical device 108 may have a diameter that is smaller than the diameter of a blood vessel. In some examples, the medical device 108 may have a diameter or thickness that is about 0.5 millimeter (mm) or less. In some examples, the medical device 108 may be a guide wire with a diameter of about 0.035 inches. In such embodiments, the transducer array 112 can produce ultrasound echoes reflected by the object 105 and the medical device 108.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed image signals. For example, the processing component 116 may perform filtering and/or quadrature demodulation to condition the image signals. The processing component 116 and/or 134 can be configured to control the array 112 to obtain ultrasound data associated with the object 105 and/or the medical device 108.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 nay be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processing component 134 is coupled to the communication interface 136. The processing component 134 may be implemented as a combination of software components and hardware components. The processing component 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105 and/or the medical device 108.

The display 132 is coupled to the processing component 134. The display 132 may be a monitor or any suitable display. The display 132 is configured to display the ultrasound images, image videos, and/or any imaging information of the object 105 and/or the medical device 108.

As described above, the system 100 may be used to provide a clinician with guidance in a medical procedure. In an example, the system 100 can capture a sequence of ultrasound images of the object 105 and the medical device 108 as the medical device 108 traverses through the object 105. The sequence of ultrasound images can be in 2D or 3D. In some examples, the system 100 may be configured to perform biplane imaging or multiplane imaging to provide the sequence of ultrasound images as biplane images or multiplane images, respectively. In some instances, the clinician may have difficulty in identifying and/or distinguishing the medical device 108 from the object 105 based on the captured images due to the motion of the medical device 108 and/or the thin geometry of the medical device 108. For example, the medical device 108 may appear to jump from one frame to another frame without time-continuity. To improve visualization, stability, and/or time-continuity of the device 108 as the device 108 moves through the object 105, the processing component 134 can apply a temporally-aware deep learning network trained for segmentation to the series of images. The deep learning network identifies and/or distinguishes the medical device 108 from the anatomical object 105 and predicts motion and/or positions of the medical device 108 using temporal information carried in the sequence of images captured across time. The processing component 134 can incorporate the prediction into the captured 2D and/or 3D image frames to provide a time series of output images with a stable view of the moving medical device 108 from frame-to-frame.

In some examples, the sequence of ultrasound images input to the deep learning network may be 3D volumes and the output prediction may be 2D images, biplane images, and/or multiplane images. In some examples, the medical device 108 may be a 2D ultrasound imaging probe and the deep learning network can be configured to predict volumetric 3D segmentation, where the sequence of ultrasound images input to the deep learning network may be 2D images, biplane images, and/or multiplane images and the output prediction may be 3D volumes.

In some examples, anatomical structures (e.g., the object 105) can be difficult to identify under 2D and/or 3D imaging due to the geometry and/or motion of the anatomical structures. For example, tortuous blood vessels in distal peripheral anatomy and/or small structures close to the heart may be affected by arterial and/or cardiac motion. Depending on the cardiac phase, the mitral leaflets and/or other structures may go in and out of an ultrasound imaging views over a time period. In another example, vessels, airways, and tumors may go in and out of an ultrasound imaging view during endobronchial ultrasound imaging, due to the breathing motion of the patient. Similarly, to improve visualization, stability, and/or time-continuity of the motion of anatomical structures, the processing component 134 can apply a temporally-aware deep learning network trained for segmentation to a series of 2D and/or 3D images of the object 105 captured across time. The deep learning network identifies and/or distinguishes the moving portion (e.g., foreground) of the object 105 from the relatively more static portion (e.g., background) of the object 105 and predicts motion and/or positions of the moving portion using temporal information carried in the sequence of images captured across time. For example, in cardiac imaging, the moving portions may correspond to mitral leaflets and the static portions may correspond to cardiac chambers, which may include relatively slower motions than valves. In peripheral vascular imaging, the moving portions may correspond to pulsatile arteries and the static portions may correspond to surrounding tissues. In lung imaging, the moving portions may correspond to lung chambers and airways and the static portions may correspond to surrounding cavities and tissues. The processing component 134 can incorporate the prediction into the captured image frames to provide a series of output images with a stable view of the moving anatomical structure from frame-to-frame. Mechanisms for providing a stable view of a moving object (e.g., the medical device 108 and/or the object 105) using a temporally-aware deep learning model are described in greater detail herein.

In an embodiment, the system 100 may be used to assist a clinician in finding an optimal imaging view of a patient for a certain clinical property or clinical examination. For example, the processing component 134 can utilize a temporally-aware deep learning network trained for image acquisition to predict an optimal imaging view or image slice of the object 105 for a certain clinical property from the captured 2D and/or 3D images. For example, the system 100 may be configured for cardiac imaging to assist a clinician in measuring a ventricular volume, determining the presence of cardiac arrhythmia, performing a trans-septal puncture, and/or provide mitral valve visualization for repair and/or replacement. The cardiac imaging can be configured to provide a four-chamber view, a three-chamber view, and/or a two-chamber view. In an example, the cardiac imaging can be used for visualizing the left ventricular overflow tract (LVOT), which may be critical for mitraclip and valve in mitral valve replacement. In an example, the cardiac imaging can be used for visualizing mitral annulus for any procedure involving annuloplasty. In an example, the cardiac imaging can be used for visualizing the left atrial appendage during a trans-septal puncture (TSP) to prevent proration. For endobronchial ultrasound imaging, the clinical property may be the presence and location of a suspected tumor and may be obtained from lateral or sagittal ultrasound views in which the ultrasound transducer is aligned with the tumor and adjacent airway tracts. In some examples, the processing component 134 can provide the clinician with instructions (e.g., rotations and/or translations) to maneuver the probe 110 from one location to another location or from one imaging plane to another imaging plane to obtain an optimal imaging view of the clinical property based on the prediction output by the deep learning network. In some examples, the processing component 134 can automate the process of reaching the optimal imaging view. For example, the processing component 134 is configured to automatically steer 2D or X-plane beams produced by the transducer array 112 to an optimal imaging location based on the prediction output by the deep learning network. An X-plane may include a cross-sectional plane and a longitudinal plane. Mechanisms for reaching an optimal imaging view using a deep learning model are described in greater detail herein.

In some embodiments, the system 100 can be used for collecting ultrasound images to form training data set for deep learning network training. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store an image data set 140 to train a temporally-aware deep learning network for image segmentations and/or imaging view guidance. Mechanisms for training a temporally-aware deep learning network are described in greater detail herein.

Figure 2:
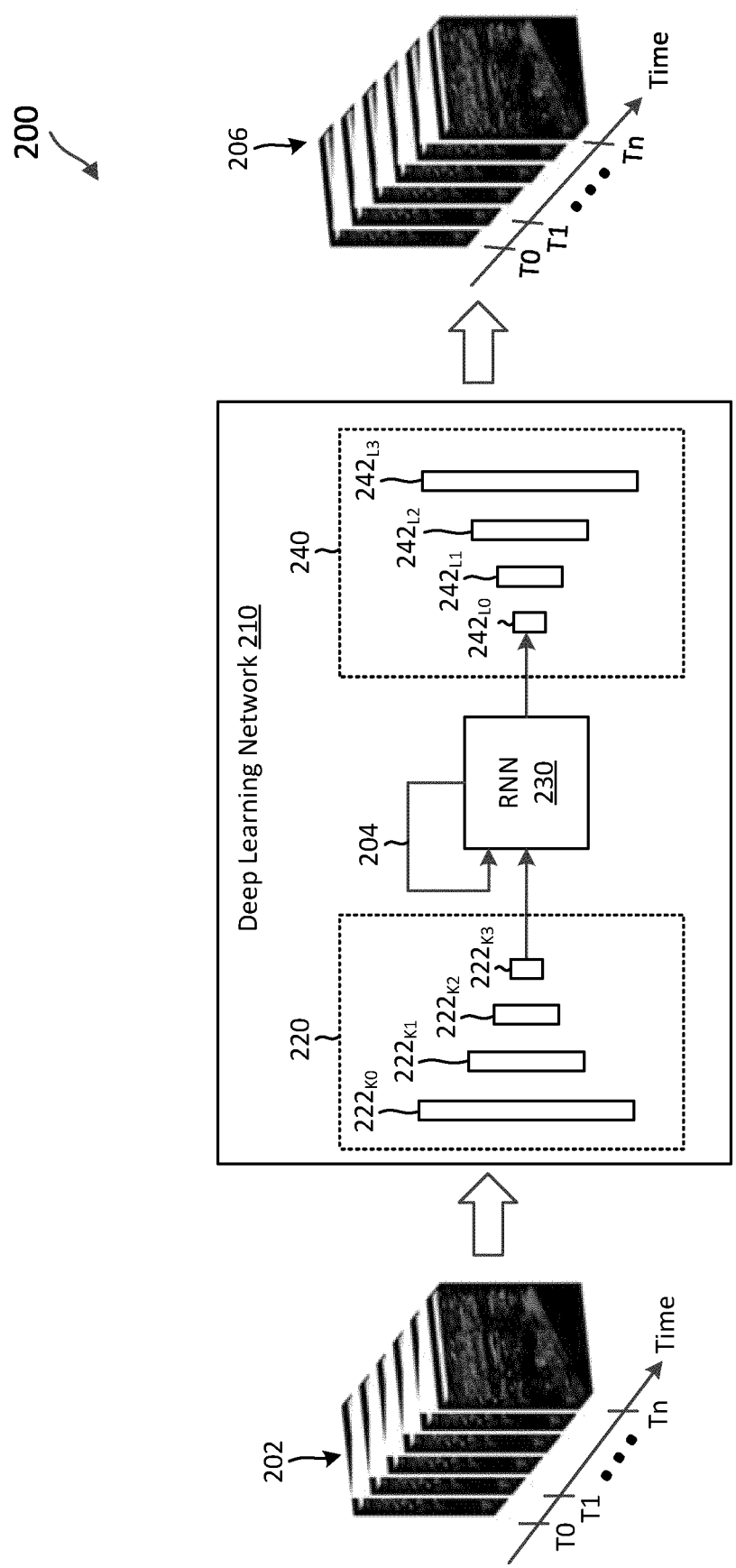
FIG. 2 is a schematic diagram of a deep learning-based image segmentation scheme, according to aspects of the present disclosure.
Figure 3:
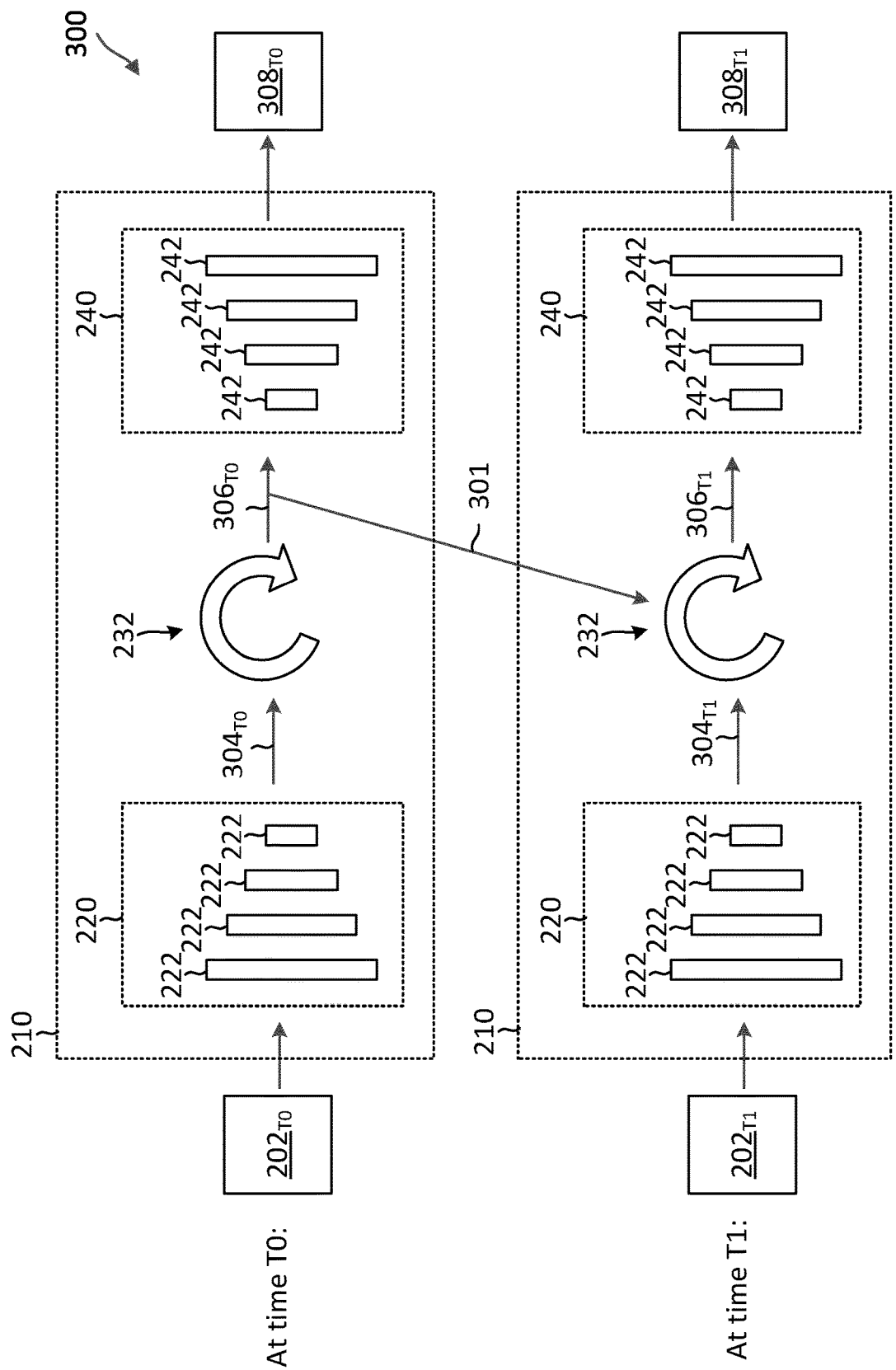
FIG. 3 is a schematic diagram illustrating a configuration for a temporally-aware deep learning network, according to aspects of the present disclosure.
Figure 4:
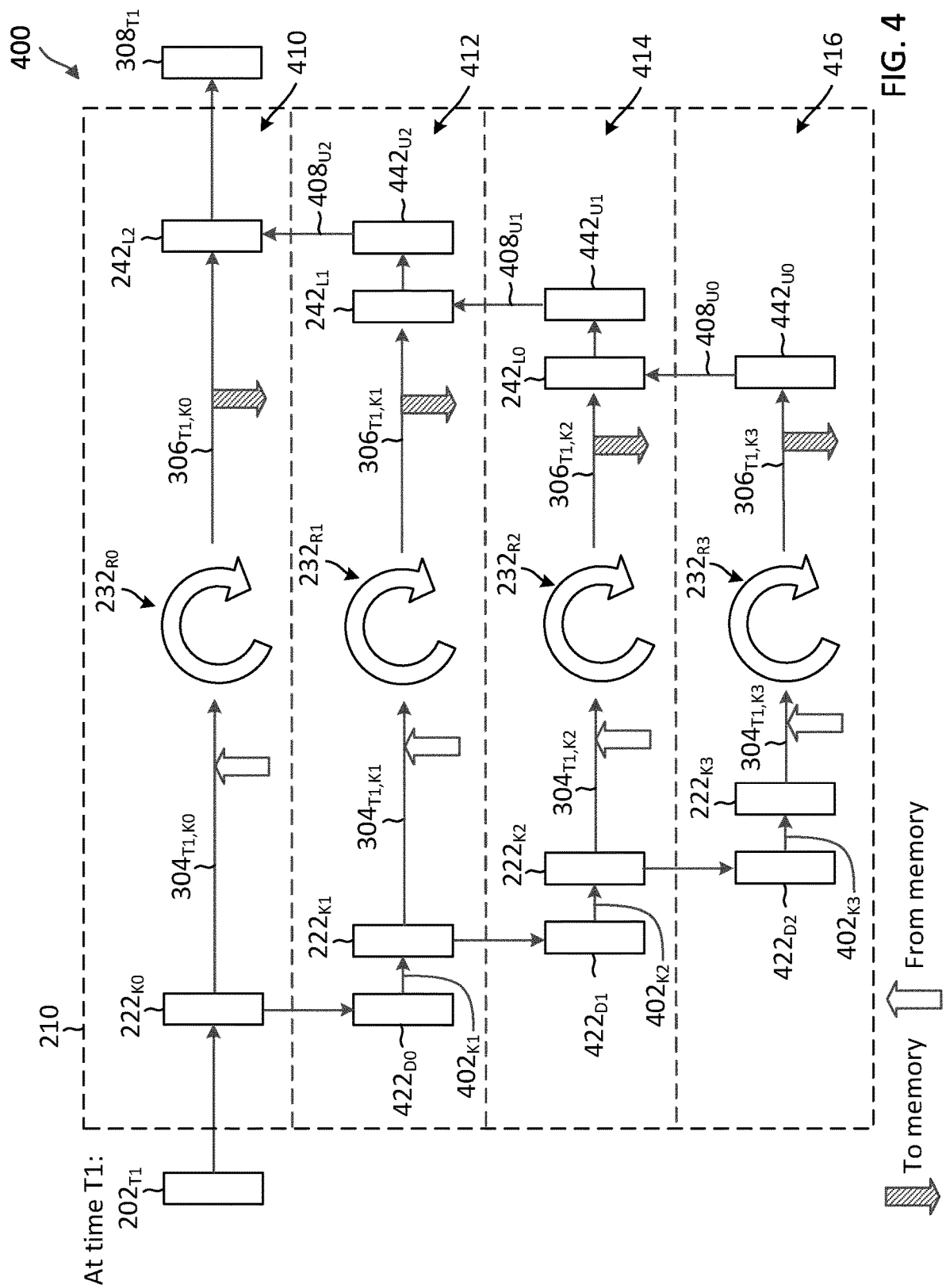
FIG. 4 is a schematic diagram illustrating a configuration for a temporally-aware deep learning network, according to aspects of the present disclosure.

FIGS. 2-4 collectively illustrate mechanisms for image segmentation using a temporally-aware multi-layered deep learning network. FIG. 2 is a schematic diagram of a deep learning-based image segmentation scheme 200, according to aspects of the present disclosure. The scheme 200 is implemented by the system 100. The scheme 200 utilizes a temporally-aware multi-layered deep learning network 210 to provide segmentations of a moving object in ultrasound images. In some examples, the moving object may be a medical device (e.g., a guide wire, a catheter, a guided catheter, a needle, or a therapy device similar to the devices 108 and/or 212) moving within a patient's anatomy (e.g., heart, lung, vessels, and/or skin similar to the object 105). In some examples, the moving object may be an anatomical structure (e.g., the object 105) with a cardiac motion, a breathing motion, and/or arterial pulses. At a high level, the multi-layered deep learning network 210 receives a sequence of ultrasound image frames 202 of the device and/or the anatomical structure. Each image frame 202 is passed through the temporally-aware multi-layered deep learning network 210. The deep learning network 210's prediction for a current image frame 202 is passed as an input for prediction of a next image frame 202. In other words, the deep learning network 210 includes a recurrent component that utilizes the temporal continuity in the sequence of ultrasound image frames 202 for prediction. Thus, the deep learning network 210 is also referred to as a recurrent predictive network.

The sequence of image frames 202 is captured across a time period (e.g., from time T0 to time Tn). The image frames 202 may be captured using the system 100. For example, the sequence of image frames 202 are reconstructed from ultrasound echoes collected by the transducer array 112, beamformed by the beamformer 114, filtered and/or conditioned by the processing components 116 and/or 134, and reconstructed by the processing component 134. The sequence of image frames 202 are input into the deep learning network 210. While FIG. 2 illustrates the image frames 202 as 3D volumes, the scheme 200 may be similarly applied to a sequence of 2D input image frames captured across time to provide segmentation. In some examples, the sequence of 3D image frames 202 across time can be referred to as a continuous 4D (e.g., 3D volumes and time) ultrasound sequence.

The deep learning network 210 includes a convolutional encoder 220, a temporally-aware RNN 230, and a convolutional decoder 240. The convolutional encoder 220 includes a plurality of convolutional encoding layers 222. The convolutional decoder 240 includes a plurality of convolutional decoding layers 242. In some examples, the number of convolutional encoding layers 222 and the number of convolutional decoding layers 242 may be the same. In some examples, the number of convolutional encoding layers 222 and the number of convolutional decoding layers 242 may be different. FIG. 2 illustrates four convolutional encoding layers $222_{K0}$, $222_{K1}$, $222_{K2}$, and $222_{K3}$ in the convolutional encoder 220 and four convolutional decoding layers $242_{L0}$, $224_{L1}$, $242_{L2}$, and $242_{L3}$ in the convolutional decoder 240 for simplicity of illustration and discussion, though it will be recognized that embodiments of the present disclosure may scale to include any suitable number of convolutional encoding layers 222 (e.g., about 2, 3, 5, 6, or more) and any suitable number of convolutional decoding layers 242 (e.g., about 2, 3, 5, 6, or more). The subscripts K0, K1, K2, and K3 represent layer indexing for the convolutional encoding layers 222. The subscripts L0, L1, L2, and L3 represent layer indexing for the convolutional decoding layers 242.

Each of the convolutional encoding layers 222 and each of the convolutional decoding layers 242 may include a convolutional filter or kernel. The convolutional kernel can be a 2D kernel or a 3D kernel depending on whether the deep learning network 210 is configured to operate on 2D images or 3D volumes. For example, when the image frames 202 are 2D images, the convolutional kernels are 2D filter kernels. Alternatively, when the image frames 202 are 3D volumes, the convolutional kernels are 3D filter kernels. The filter coefficients for the convolutional kernels are trained to learn segmentation of moving objects as described in greater detail herein.

In some embodiments, the convolutional encoding layers 222 and the convolutional decoding layers 242 may operate at multiple different spatial resolutions. In such embodiments, each convolutional encoding layer 222 may be followed by a down-sampling layer. Each convolutional decoding layer 242 can be preceded by an up-sampling layer. The down-sampling and up-sampling can be at any suitable factor. In some examples, the down-sampling factor at each down-sampling layer and the up-sampling factor at each up-sampling layer can be about 2. The convolutional encoding layers 222 and the convolutional decoding layers 242 can be trained to extract features from the sequence of image frames 202 at different spatial resolutions.

The RNN 230 is positioned between the convolutional encoding layers 222 and the convolutional decoding layers 242. The RNN 230 is configured to capture temporal information (e.g., temporal continuity) from the sequence of input image frames 202 for segmentation of moving objects. The RNN 230 may include multiple temporally-aware recurrent components (e.g., the recurrent component 232 of FIGS. 3 and 4). For example, the RNN 230 passes a prediction for a current image frame 202 (captured at time T0) back to the RNN 230 as a secondary input for a prediction for a next image frame 202 (captured at time T1) as shown by the arrow 204. The use of temporal information at different spatial resolutions for segmentation of moving objects is described in greater detail below with respect to FIGS. 3 and 4.

FIG. 3 is a schematic diagram illustrating a configuration 300 for the temporally-aware deep learning network 210, according to aspects of the present disclosure. FIG. 3 provides a more detailed view of the use of temporal information at the deep learning network 210. For simplicity of illustration and discussion, FIG. 3 illustrates operations of the network 210 at two time instants, T0 and T1. However, similar operations may be propagated to subsequent time T2, T3, . . . , and Tn. Additionally, the convolutional encoding layers 222 are shown without the layer indexing subscripts K0, K1, K2, and K3 and the convolutional decoding layers 242 are shown without the layer indexing subscripts L0, L1, L2, and L3 for simplicity sake. FIG. 3 uses subscripts T0 and T1 to represent time indexing.

At time T0, the system 100 captures an image frame $202_{T0}$. The image frame $202_{T0}$ is input into the deep learning network 210. The image frame $202_{T0}$ is processed by each of the convolutional encoding layers 222. The convolutional encoding layers 222 produces encoded features $304_{T0}$. The encoded features $304_{T0}$ may include features at different spatial resolutions as described in greater detail herein below.

The RNN 230 may include multiple recurrent components 232, each operating at one of the spatial resolutions. In some examples, the recurrent component 232 may be long short-term memory (LSTM) units. In some examples, the recurrent component 232 may be gated recurrent components (GRUs). Each recurrent component 232 is applied to the encoded features $304_{T0}$ of a corresponding spatial resolution to produce output $306_{T0}$. The output $306_{T0}$ are stored in a memory (e.g., the memory 138). In some examples, the recurrent component 232 can include a single convolutional operation per feature channel.

The output $306_{T0}$ is subsequently processed by the each of the convolutional decoding layers 242 to produce a confidence map $308_{T0}$. The confidence map $308_{T0}$ predicts whether a pixel of the image includes the moving object. In an example, the confidence map $308_{T0}$ may include a value between about 0 to about 1 representing the likelihood of a pixel including a moving object, where a value closer to 1 represents a pixel that is likely to include the moving object and a value closer to 0 represents a pixel that is less likely to include the moving object. Alternatively, a value closer to 1 may represent a pixel that is less likely to include the moving object and a value closer 0 represents a pixel that is likely to include the moving object. In general, for each pixel, the confidence map $308_{T0}$ may indicate a probability or confidence level of the pixel including the moving object. In other words, the confidence map $308_{T0}$ can provide prediction of the moving object's position and/or motion in each image frame 202 in the sequence.

At time T1, the system 100 captures the image frame $202_{T1}$. The deep learning network 210 may apply the same operations to the image frame $202_{T1}$ as the image frame $202_{T0}$. However, the encoded features $304_{T1}$ produced by each convolutional encoding layer 222 are concatenated with the output $306_{T0}$ from the previous time T0 (as shown by the arrow 301) before being passed to the convolutional decoding layers 242. The concatenation of passed output $306_{T0}$ and current encoded features $304_{T1}$ is performed at each spatial resolution layer. The concatenation of the previous output $306_{T0}$ at time T0 and the current encoded features $304_{T0}$ at each spatial resolution layer allows the recurrent part of the network 210 to have full exposure to features at every past time point and every spatial resolution level (e.g., from coarse to fine) before making a prediction on the input image frame $202_{T1}$ at the current time T1. The capturing of temporal information at each spatial resolution layer is described in greater detail below with respect to FIG. 4.

FIG. 4 is a schematic diagram illustrating a configuration 400 for the temporally-aware deep learning network 210, according to aspects of the present disclosure. FIG. 4 provides a more detailed view of the internal operations at the deep learning network 210. For simplicity of discussion and illustration, FIG. 4 illustrates the operations of the deep learning network 210 on a single input image frame 202 (e.g., at time T1). However, similar operations may be applied to each image frame 202 in the sequence. Additionally, the operations are shown for four different spatial resolutions 410, 412, 414, and 416. However, similar operations may be applied for any suitable number of spatial resolutions (e.g., about 2, 3, 5, 6, or more). FIG. 4 provides an expanded view of the RNN 230. As shown, the RNN 230 includes a recurrent component 232 at each spatial resolution 410, 412, 414, and 416 to capture temporal information at each spatial resolution 410, 412, 414, and 416. The recurrent components 232 are shown as $232_{R0}$, $232_{R1}$, $232_{R2}$, and $232_{R3}$ for the spatial resolutions 410, 412, 414, and 416, respectively. Additionally, each of the convolutional encoding layer 222 is followed by a down-sampling layer 422 and each of the convolutional decoding layer 242 is preceded by an up-sampling layer 442.

At time T1, the image frame $202_{T1}$ is captured and input into the deep learning network 210. The image frame $202_{T1}$ is passed through each of the convolutional encoding layers $222_{K0}$, $222_{K1}$, $222_{K2}$, and $222_{K3}$. The image frame $202_{T1}$ may have a spatial resolution 410. As shown, the image frame $202_{T1}$ is convolved with the convolutional encoding layer $222_{K0}$ to output encoded features $304_{T1,K0}$ (e.g., in the form of a tensor) at the spatial resolution 410. The output of the convolutional encoding layers $222_{K0}$ is down-sampled by the down-sampling layer $422_{D0}$ to produce a tensor $402_{D0}$ at the spatial resolution 412. The tensor $402_{D0}$ is convolved with the convolutional encoding layer $222_{K1}$ to output encoded features $304_{T1,K1}$ at the spatial resolution 412. The output of the convolutional encoding layers $222_{K1}$ is down-sampled by the down-sampling layer $422_{D1}$ to produce a tensor $402_{D1}$ at the spatial resolution 414. The tensor $402_{D1}$ is convolved with the convolutional encoding layer $222_{K2}$ to output encoded features $304_{T1,K2}$ at the spatial resolution 414. The output of the convolutional encoding layers $222_{K2}$ is down-sampled by the down-sampling layer $422_{D2}$ to produce a tensor $402_{D2}$ at the spatial resolution 416. The tensor $402_{D2}$ is convolved with the convolutional encoding layer $222_{K3}$ to output encoded features $304_{T1,K3}$ at the spatial resolution 416.

Temporal continuity information is captured at each of the spatial resolution 410, 412, 414, and 416. At the spatial resolution 410, the encoded features $304_{T1,K0}$ are concatenated with an output $306_{T0,K0}$ of the recurrent component $232_{R0}$ obtained at a previous time T0 for the convolutional encoding layer $222_{K0}$. For example, the previous output $306_{T0,K0}$ is stored in a memory (e.g., the memory 138) at time T0 and retrieved from the memory for processing at time T1. The retrieval of the previous recurrent component output $306_{T0,K0}$ from the memory is shown by the empty-filled arrow. The recurrent component $232_{R0}$ is applied to the concatenation of the encoded features $304_{T1,K0}$ and the output $306_{T0,K0}$ to produce an output $306_{T1,K0}$. In some examples, the output $306_{T1,K0}$ can be down-sampled so that the output $306_{T1,K0}$ may have the same dimensions as the encoded feature $304_{T1,K0}$. The output $306_{T1,K0}$ is stored in the memory (shown by the pattern-filled arrow) and can be retrieved for a similar concatenation at a next time T2.

Similarly, at the spatial resolution 412, the encoded features $304_{T1,K1}$ are concatenated with an output $306_{T0,K1}$ of the recurrent component $232_{R1}$ obtained at the previous time T0. The recurrent component $232_{R1}$ is applied to the concatenation of the encoded features $304_{T1,K1}$ and the output $306_{T0,K1}$ to produce an output $306_{T1,K1}$. The output $306_{T1,K1}$ is stored in the memory (shown by the pattern-filled arrow) for a similar concatenation at the next time T2.

At the spatial resolution 414, the encoded features $304_{T1,K2}$ are concatenated with an output $306_{T0,K2}$ of the recurrent component $232_{R2}$ obtained at the previous time T0. The recurrent component $232_{R2}$ is applied to the concatenation of the encoded features $304_{T1,K2}$ and the output $306_{T0,K2}$ to produce an output $306_{T1,K2}$. The output $306_{T1,K2}$ is stored in the memory (shown by the pattern-filled arrow) for a similar concatenation at the next time T2.

At the last spatial resolution 416, the encoded features $304_{T1,K3}$ are concatenated with an output $306_{T0,K2}$ of the recurrent component $232_{R3}$ obtained at the previous time T0. The recurrent component $232_{R3}$ is applied to the concatenation of the encoded features $304_{T1,K3}$ and the output $306_{T0,K3}$ to produce an output $306_{T1,K3}$. The output $306_{T1,K3}$ is stored in the memory (shown by the pattern-filled arrow) for a similar concatenation at the next time T2.

The outputs $306_{T1,K3}$, $306_{T1,K2}$, $306_{T1,K1}$, and $306_{T1,K0}$, are passed to the convolutional decoding layers $242_{L0}$, $242_{L1}$, and $242_{L2}$, respectively. For example, the output $306_{T1,K3}$ is up-sampled by the up-sampling layer $442_{U0}$ to produce a tensor $408_{U0}$ (e.g., including extracted features. The tensor $408_{U0}$ and the output $306_{T1,K2}$ are convolved with the convolutional decoding layers $242_{L0}$ and up-sampled by the up-sampling layer $442_{U1}$ to produce a tensor $408_{U1}$. The tensor $408_{U1}$ and the output $306_{T1,K1}$ are convolved with the convolutional decoding layers $242_{L1}$ and up-sampled by the up-sampling layer $442_{U2}$ to produce a tensor $408_{U2}$. The tensor $408_{U2}$ and the output $306_{T1,K0}$ are convolved with the convolutional decoding layers $242_{L2}$ to produce the confidence map $308_{T1}$. While FIG. 4 illustrates four encoding layers 222 and three decoding layers 242, the network 210 can be alternatively configured to include four decoding layers 242 to provide similar predictions. In general, the encoder (shown in the left side the network 210 in FIG. 4) is where the learning process occurs. The number of encoding layers 222 can be determined based on the size of the input volume and the receptive field of the network 210. The depth of the network 210 can be varied based on how large the input image is and its influence on learning the features i.e. by controlling the receptive field of the network 210. As such, the network 210 may not have a corresponding decoder/up-sampling layer to the innermost layer. The decoder (shown in the right side of the network 210 in FIG. 4) takes the features from lower resolution feature maps and assembles them, while up-sampling towards the original output size As can be observed, the deep learning network 210 performs prediction for a current image frame 202 (at time Tn) based on features extracted from the current image frame 202 and the previous image frame 202 (at time Tn-1) instead of based on a single image frame captured at a single point of time. The deep learning network 210 can infer motion and/or positional information associated with a moving object based on information in the past. The time-continuity information (e.g., provided by the temporal concatenation) can provide additional dimensionality information. The use of temporal information can be particular useful in segmenting a thin object since a thin object may typically be represented by a relatively less number of pixels in an imaging frame than a thicker object. Accordingly, the present disclosure can improve visualization and/or stability in ultrasound images and/or videos of a moving medical device and/or an anatomical structure including a moving portion.

The down-sampling layers 422 can perform down-sampling at any suitable down-sampling factor. In an example, each down-sampling layers 422 may perform down-sampling by a factor of 2. For example, the input image frame $202_{T1}$ has a resolution of 200×200×200 voxels (e.g., the spatial resolution 410). The input image frame $202_{T1}$ is down-sampled by 2 to produce the tensor $402_{D0}$ at a resolution of 100×100×100 voxels (e.g., the spatial resolution 412). The tensor $402_{D0}$ is down-sampled by 2 to produce the tensor $402_{D1}$ at a resolution of 50×50×50 voxels (e.g., the spatial resolution 414. The tensor $402_{D1}$ is down-sampled by 2 to produce the tensor $402_{D2}$ at a resolution of 25×25×25 voxels (e.g., the spatial resolution 416). The up-sampling layers 442 may reverse the down-sampling. For example, each of the up-sampling layers 442 may performing up-sampling by a factor of 2. In some other examples, the down-sampling layers 422 may perform down-sampling at different down-sampling factors and the up-sampling layers 442 may perform up-sampling using factors matching to the down-sampling factors. For example, the down-sampling layers $422_{D0}$, $422_{D1}$, and $422_{D2}$ may perform down-sampling by 2, 4, and 8, respectively, and the up-sampling layers $442_{U0}$, $442_{U1}$, and $442_{U2}$ may perform up-sampling by 8, 4, and 2, respectively.

The convolutional encoding layers 222 and the convolutional decoding layers 242 may include convolutional kernels of any sizes. In some examples, the kernel sizes may be dependent on the size of the input image frames 202 and can be selected to limit the network 210 to a certain complexity. In some examples, each of the convolutional encoding layers 222 and each of the convolutional decoding layers 242 may include a 5×5×5 convolutional kernel. In an example, the convolutional encoding layer $222_{K0}$ may provide about one feature (e.g., the feature $304_{T1,K0}$ has a size of 1) at the spatial resolution 410. The convolutional encoding layer $222_{K1}$ may provide about two features (e.g., the feature $304_{T1,K1}$ has a size of 2) at the spatial resolution 412. The convolutional encoding layers $222_{1<2}$ may provide about four features (e.g., the feature $304_{T1,K2}$ has a size of 4) at the spatial resolution 414. The convolutional encoding layer $222_{K3}$ may provide about eight features (e.g., the feature $304_{T1,K3}$ has a size of 8) at the spatial resolution 416. In general, the number of features may increase as the spatial resolution decreases.

In some embodiments, the convolutions at the convolutional encoding layers 222 and/or the convolutional decoding layers 242 can be repeated. For example, the convolution at the convolutional encoding layers $222_{K0}$ can be repeated twice, the convolution at the convolutional encoding layers $222_{K1}$ can be performed once, the convolution at the convolutional encoding layers $222_{K2}$ can be repeated twice, and the convolution at the at the convolutional encoding layers $222_{K3}$ can be repeated twice.

In some embodiments, each of the convolutional encoding layers 222 and/or each of the convolutional decoding layers 242 can include a non-linear function (e.g., a parametric rectified linear unit (PReLu)).

In some examples, each of the recurrent components 232 may include a convolutional gated recurrent component (convGRU). In some examples, each of the recurrent components 232 may include a convolutional long short-term memory (convLSTM).

While FIG. 4 illustrates the propagation of temporal information over two points of time (e.g., from T0 to T1 or from T1 to T2), in some examples, the temporal information can be propagated over a greater number of time points (e.g., about 3 or 4).

Returning to FIG. 2, the deep learning network 210 may output a confidence map 308 for each image frame 202. As described above, for each pixel in an image frame 202, a corresponding confidence map 308 can include a probability or a confidence level of the pixel including the moving object. A sequence of output image frames 206 can be generated based on the sequence of input image frames 202 and corresponding confidence maps 308. In some examples, temporally-aware inferencing can interpolate or otherwise predict missing image information of the moving object based on the confidence map 308. In some examples, the inference, interpolation, and/or prediction can be implemented outside of the deep learning network 210. In some examples, the interpolation and/or the reconstruction can be implemented as part of the deep learning network 210. In other words, the learning and training of the deep learning network 210 may include the inference, interpolation, and/or prediction of missing imaging information.

In an embodiment, the deep learning network 210 can be trained to differentiate an elongate flexible thin moving medical device (e.g., a guide wire, a guided catheter, a catheter, a needle, a therapy device, and/or a treatment device) from an anatomy. For example, a training data set (e.g., the image data set 140) can be created for the training using the system 100. The training data set can include input-output pairs. For each input-output pair, the input may include a sequence of image frames (e.g., 2D or 3D) of a medical device (e.g., the device 108) traversing across an anatomy (e.g., the object 105) across time and the output may include ground truths or annotations of the positions of the medical device within each image frame in the sequence. In an example, the ground truth position of the medical device can be obtained by attaching an ultrasound sensor to the medical device (e.g., at the tip of the medical device) during imaging and subsequently fitting a curve or spline to the captured images using at least the tip as an end point constraint for the spline. After fitting the curve to the ultrasound images, the images can be annotated or labelled with the ground truths for training. During training, the deep learning network 210 can be applied to the sequence of image frames using forward propagation to produce an output. The coefficients of the convolutional kernels at the convolutional encoding layers 222, the recurrent components 232, and/or the convolutional decoding layers 242 can be adjusted using backward propagation to minimize an error between the output and the ground truth positions of the device. The training process can be repeated for each input-output pair in the training data set.

In another embodiment, the deep learning network 210 can be trained to differentiate a moving portion of an anatomy from a static portion of the anatomy using a training data set (e.g., the image date set 140). For example, a training data set (e.g., the image date set 140) can be created for the training using the system 100. The training data set can include input-output pairs. For each input-output pair, the input may include a sequence of image frames (e.g., 2D or 3D) of an anatomy with motion (e.g., associated with cardiac, breathing, and/or arterial pulses) and the output may include ground truths or annotations of the various moving and/or static portions of the anatomy. The ground truths and/or annotations can be obtained from various annotated data sets that are available to the medical community. Alternatively, the sequence of image frames can be annotated manually with the ground truths. After obtaining the training data set, similar mechanisms as described above (e.g., for the moving object) may be used to the train the deep learning network 210 for segmenting moving anatomical structures.

FIGS. 5-8 illustrate various clinical use case scenarios where the temporally-aware deep learning network 210 can be used to provide improved segmentation based on a series of observations over time.

Figure 5:
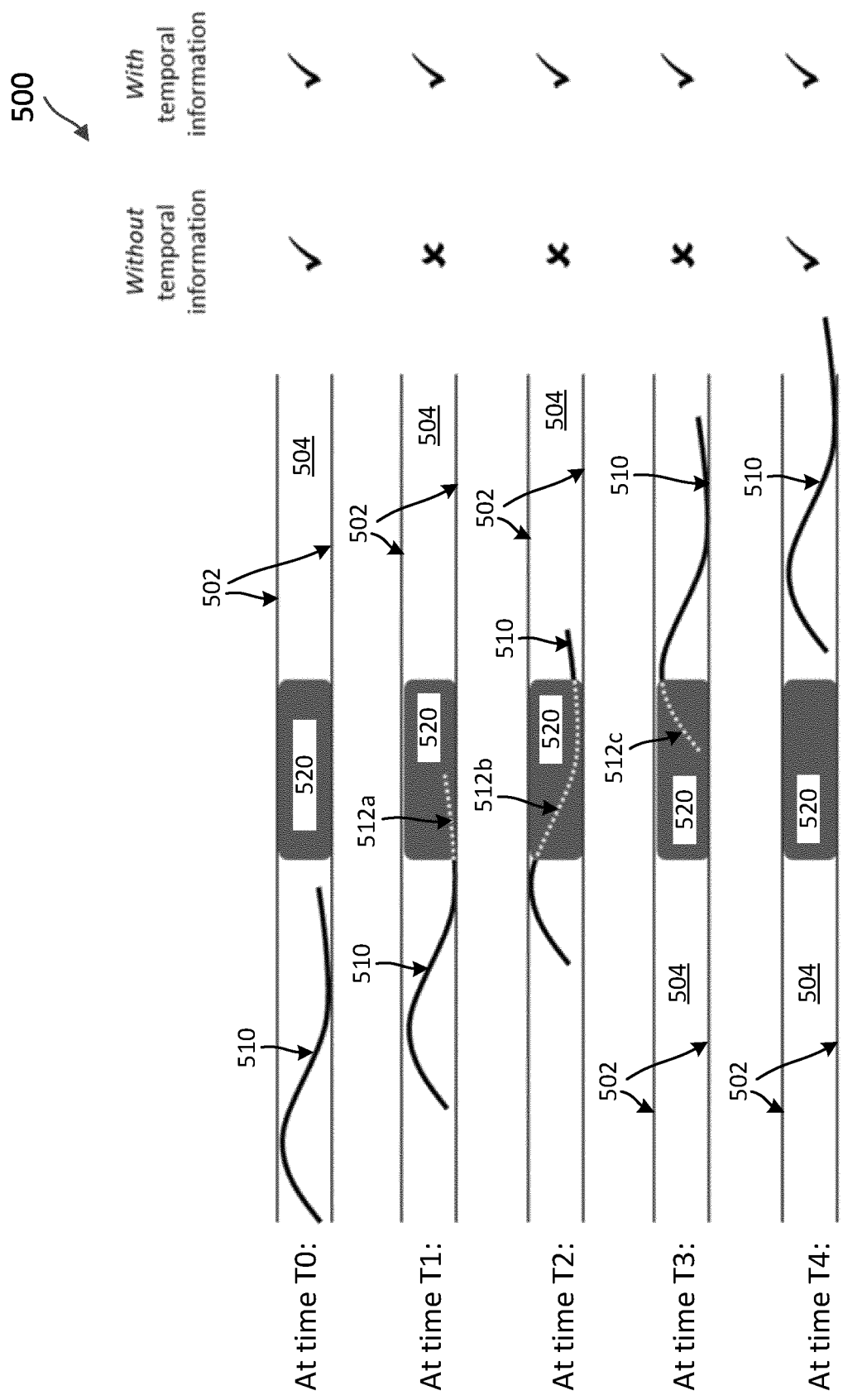
FIG. 5 illustrates a scenario of an ultrasound-guided procedure, according to aspects of the present disclosure.

FIG. 5 illustrates a scenario 500 of an ultrasound-guided procedure, according to aspects of the present disclosure. The scenario 500 may correspond to a scenario when the system 100 is used to capture ultrasound images of a thin guide wire 510 (e.g., the medical device 108) passing through a vessel lumen 504 with a vessel wall 502 including an occluded region 520 (e.g., plaque and/or calcification). For example, a sequence of ultrasound images is captured at time T0, T1, T2, T3, and T4. The columns in the right side of FIG. 5 include checkmarks and crosses. The checkmarks indicate that the guide wire 510 is fully visible in a corresponding image frame. The crosses indicate that the guide wire 510 is not fully visible in a corresponding image frame.

At time T0, the guide wire 510 enters the lumen 504. At time T1, a beginning portion 512a of the guide wire 510 (shown by the dashed line) enters the occluded region 520. At time T2, the guide wire 510 continues to pass through the lumen 504, where a middle portion 512b of the guide wire 510 (shown by the dashed line) is within the occluded region 520. At time T3, the guide wire 510 continues to pass through the lumen 504, where an end portion 512c of the guide wire 510 (shown by the dashed line) is within the occluded region 520. At time T4, the guide wire 510 exits the occluded region 520.

General 3D segmentation without utilizing temporal information may fail to segment the portions 512a, 512b, and 512c within the occluded region 520 at time T1, T2, and T3, respectively. Thus, the image frames obtained at time T1, T2, and T3 without temporal information may each include a missing segment, section, or portion of the guide wire 510 corresponding to the portions 512a, 512b, and 512c within the occluded region 520, respectively. As such, crosses are shown for time T1, T2, and T3 under the column for segmentation without temporal information.

The temporally-aware deep learning network 210 is designed to interpolate the missing information based on previous image frames, and thus the system 100 can apply the deep learning network 210 to infer the missing portions 512a, 512b, and 512c in the images. As such, checkmarks are shown for time T1, T2, and T3 under the column for segmentation with temporal information.

In some examples, the scenario 500 may be similar to a peripheral vascular intervention procedure, where the occluded region 520 may correspond to a chronic total occlusion (CTO) crossing in peripheral vascular structure. In some examples, the scenario 500 may be similar to a clinical procedure where a tracking device passes through air gaps, calcifications, or regions of shadowing (e.g., the occluded region 520).

Figure 6:
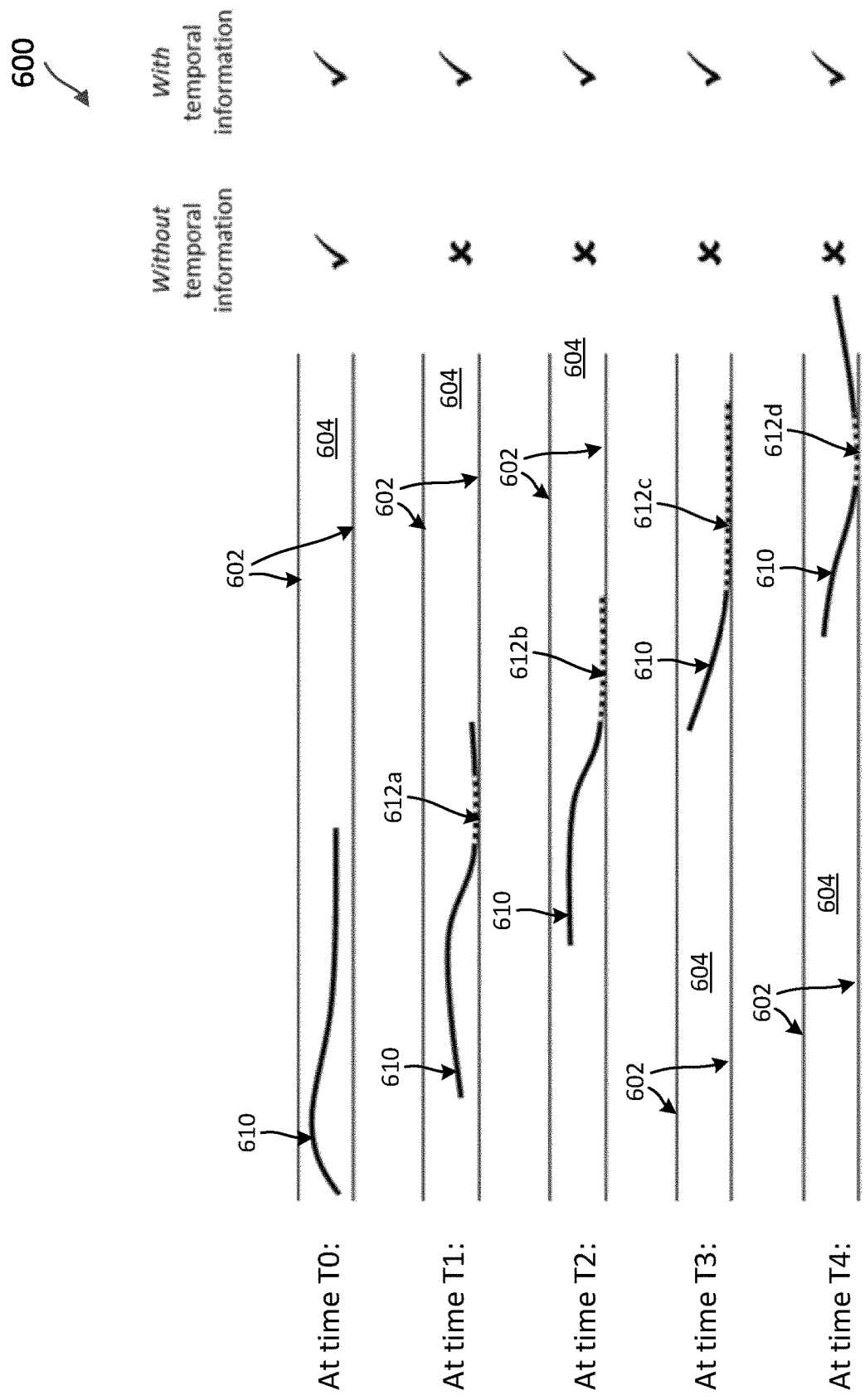
FIG. 6 illustrates a scenario of an ultrasound-guided procedure, according to aspects of the present disclosure.

FIG. 6 illustrates a scenario 600 of an ultrasound-guided procedure, according to aspects of the present disclosure. The scenario 600 may correspond to a scenario when the system 100 is used to capture ultrasound images of a guide wire 610 (e.g., the medical device 108) passing through a vessel lumen 604 with a vessel wall 602, where the guide wire 610 may glide along the vessel wall 602 for a period of time. For example, a sequence of ultrasound images is captured at time T0, T1, T2, T3, and T4. The columns in the right side of FIG. 6 include checkmarks and crosses. The checkmarks indicate that the guide wire 610 is fully visible in corresponding image frames. The crosses indicate that the guide wire 610 is not fully visible in corresponding image frames.

At time T0, the guide wire 610 initially enters the lumen 604 at about a center of the lumen 604. At time T1, a portion 612a of the guide wire 610 (shown by the dashed line) slides against the vessel wall 602. The guide wire 610 continues to slide against the vessel wall 602. As shown, at time T2, a portion 612b of the guide wire 610 (shown by the dashed line) is adjacent to the vessel wall 602. At time T3, a portion 612c of the guide wire 610 (shown by the dashed line) is adjacent to the vessel wall 602. At time T4, a portion 612d of the guide wire 610 (shown by the dashed line) is adjacent to the vessel wall 602.

The guide wires 610 may be similarly reflective as the vessel wall 602, and thus general 3D segmentation without utilizing temporal information may fail to segment the portions 612a, 612b, 612c, 612d that are close to the vessel wall 602 at time T1, T2, T3, and T4, respectively. Thus, the image frames obtained at time T1, T2, T3, and T4 without temporal information may each include a missing section, segment, or portion of the guide wire 610 corresponding to the portions 612a, 612b, 612c, and 612d, respectively. As such, crosses are shown for time T1, T2, T3, and T4 under the column for segmentation without temporal information.

The temporally-aware deep learning network 210 is exposed to the entire sequence of ultrasound image frames or video frames across time, and thus may be applied to the sequence of images to predict the positions and/or motion of the portions 612a, 612b, 612c, and 612d close to the vessel wall 602 at time T1, T2, T3, and T4, respectively. Thus, checkmarks are shown for time T1, T2, T3, and T4 under the column for segmentation with temporal information.

In some examples, the scenario 600 may be similar to a cardiac imaging procedure where a medical device or a guide wire glides along the wall of a cardiac chamber. In some examples, the scenario 600 may be similar to a peripheral vascular intervention procedure where a subintimal is purposefully directed to into the adventitia of a vessel wall in order to bypass occlusions.

Figure 7:
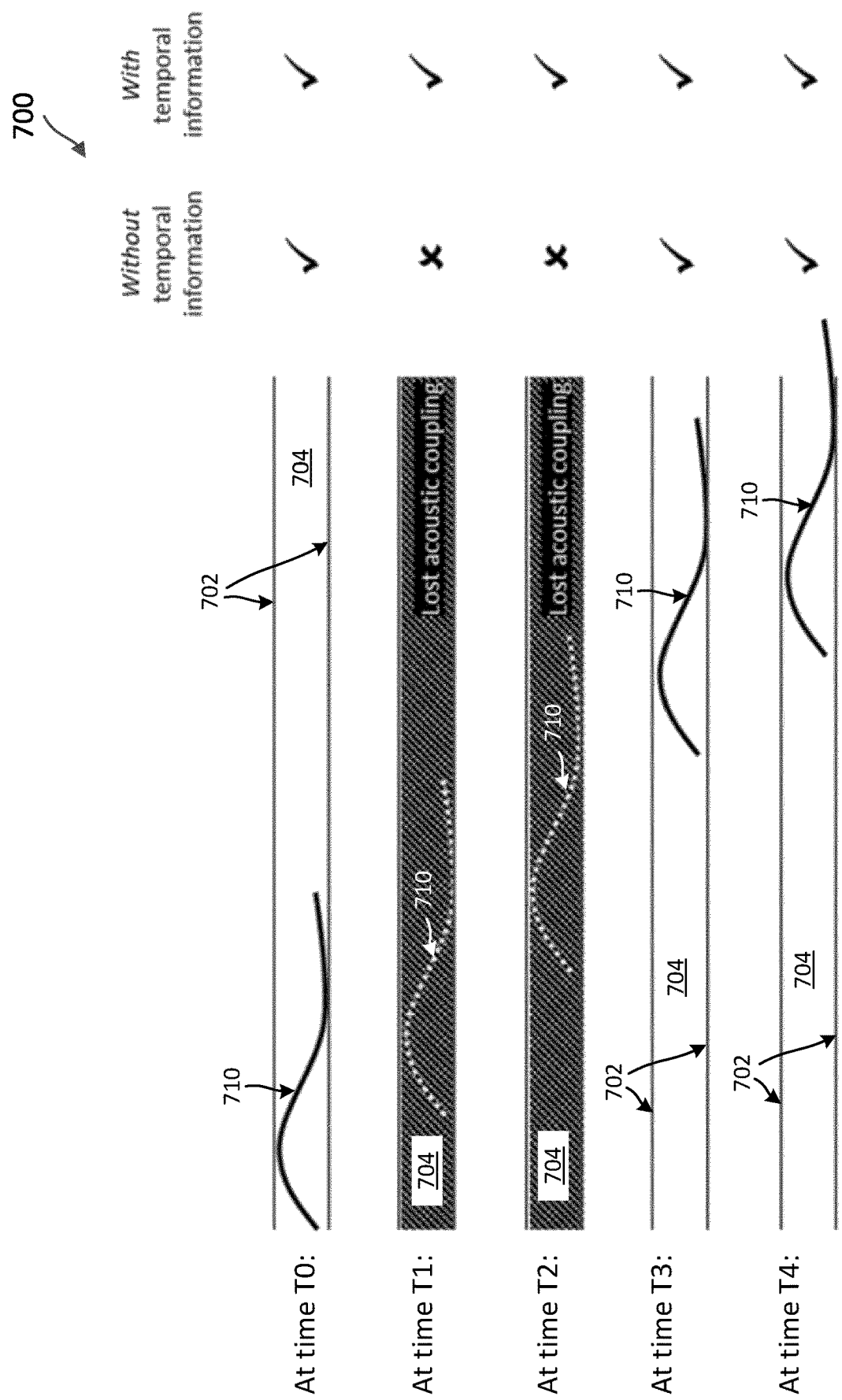
FIG. 7 illustrates a scenario of an ultrasound-guided procedure, according to aspects of the present disclosure.

FIG. 7 illustrates a scenario 700 of an ultrasound-guided procedure, according to aspects of the present disclosure. The scenario 700 may correspond to a scenario when the system 100 is used to capture ultrasound images of a guide wire 710 (e.g., the medical device 108) passing through a vessel lumen 704 with a vessel wall 702, where acoustic coupling is lost for a period of time. For example, a sequence of ultrasound images is captured at time T0, T1, T2, T3, and T4. The columns in the right side of FIG. 7 include checkmarks and crosses. The checkmarks indicate that the guide wire 710 is fully visible in a corresponding image frame. The crosses indicate that the guide wire 710 is not fully visible in a corresponding image frame.

At time T0, the guide wire 710 enters the lumen 704. The acoustic coupling is lost at time T1 and T2. The acoustic coupling is regained at time T3. General 3D imaging without utilizing temporal information may lose all knowledge of the positions of the guide wire 610 when acoustic coupling is lost. Thus, the guide wire 710 may not be visible in image frames obtained at time T1 and T2 without temporal information. As such, crosses are shown for time T1 and T2 under the column for segmentation without temporal information.

The temporally-aware deep learning network 210 has the capacity to remember the location of the guide wire 710 for at least a few frames, and thus can be applied to the sequence of images to predict the locations of the guide wire 710 at time T1 and time T2. Thus, checkmarks are shown for time T1 and T2 under the column for segmentation with temporal information. If the acoustic coupling is lost for an extended period of time, the temporally-aware deep learning network 210 is less likely to produce incorrect segmentation results.

The scenario 700 may occur whenever acoustic coupling is lost. It may be difficult to maintain acoustic coupling at all time during imaging. Thus, the temporally-aware deep learning-based segmentation can improve visualization of various device and/or anatomical structures in ultrasound images, especially when automation is involved, for example, during automatic beam steering, sensor tracking with image-based constraints, and/or robotic control of ultrasound imaging device. In other scenario, for example, acoustic coupling may be lost for a short period of time during cardiac imaging due to the motion of the hearts. Thus, the temporally-aware deep learning-based segmentation can improve visualization in cardiac imaging.

Figure 8:
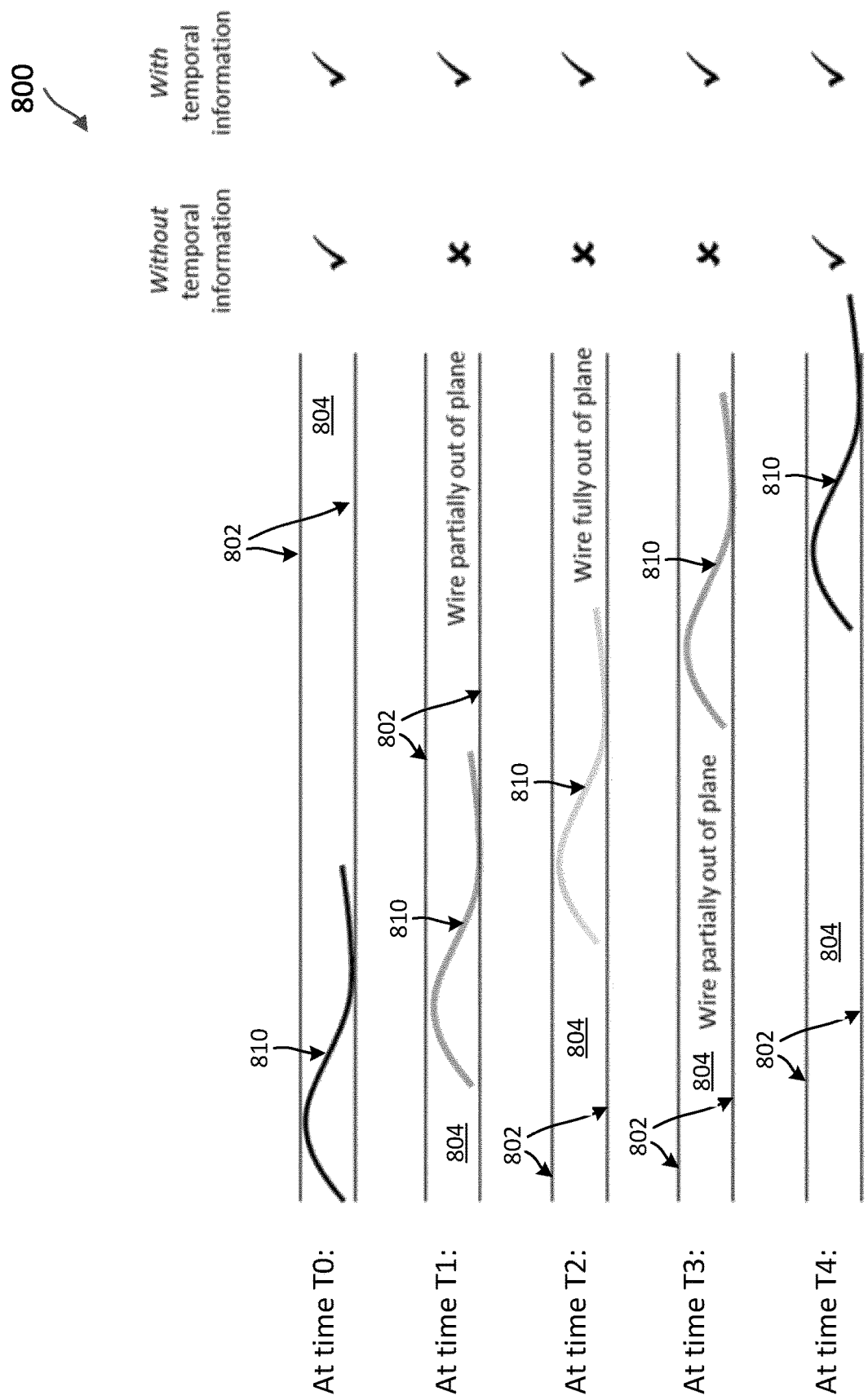
FIG. 8 illustrates a scenario of an ultrasound-guided procedure, according to aspects of the present disclosure.

FIG. 8 illustrates a scenario 800 of an ultrasound-guided procedure, according to aspects of the present disclosure. The scenario 800 may correspond to a scenario when the system 100 is used to capture ultrasound images of a guide wire 810 (e.g., the medical device 108) passing through a vessel lumen 804 with a vessel wall 802, where the guide wire 810 may go in and out of plane during imaging. For example, a sequence of ultrasound images is captured at time T0, T1, T2, T3, and T4. The columns in the right side of FIG. 8 include checkmarks and crosses. The checkmarks indicate that the guide wire 810 is fully visible in a corresponding image frame. The crosses indicate that the guide wire 810 is not fully visible in a corresponding image frame.

At time T0, the guide wire 810 enters the lumen 804 and is in plane under the imaging. At time T1, the guide wire 810 starts to drift out of plane (e.g., partially out-of-plane). At time T2, the guide wire 810 is fully out of plane. At time T3, the guide wire 810 continues to drift and is partially out of plane. At time T4, the guide wire 810 moves back in plane. General 3D imaging without utilizing temporal information may not detect any structure that is out of plane. Thus, the guide wire 810 may not be fully visible in the image frames obtained at time T1, T2, and T3 without temporal information. As such, crosses are shown for time T1, T2, and T3, under the column for segmentation without temporal information.

The temporally-aware deep learning network 210 is able to predict out-of-plane device position to provide full visibility of the device, and thus can be applied to the sequence of images to predict the locations of the guide wire 810. Thus, checkmarks are shown for time T1, T2, and T3 under the column for segmentation without temporal information).

In some examples, the scenario 800 may occur in an ultrasound-guided procedure where non-volumetric imaging mode (e.g., 2D imaging) is used. In some examples, the scenario 800 may occur in real-time 3D imaging where relatively small-sized 3D volumes are acquired in in a transverse direction in order to maintain a sufficiently high frame rate. In some examples, the scenario 800 may occur in cardiac imaging where the motion of a heart may cause the certain portions of the heart to enter and exit an imaging plane.

While the scenarios 500-800 illustrate the use of the temporally-aware deep learning network 210 for providing segmentation of a moving guide wire (e.g., the guide wires 510, 610, 710, and/or 810), similar temporally-aware deep learning-based segmentation mechanisms can be applied to any elongate flexible, thinly-shaped moving devices (e.g., catheters, guided catheters, needles, IVUS devices, and/or therapy device) and/or anatomical structures with moving portions. In general, temporally-aware deep learning-based segmentation can be used to improve visualization and/or stability of moving devices and/or anatomy with motion under imaging. In other words, the temporally-aware deep learning-based segmentation can minimize or remove discontinuity in motions of moving devices and/or moving anatomical structures.

Figure 9:
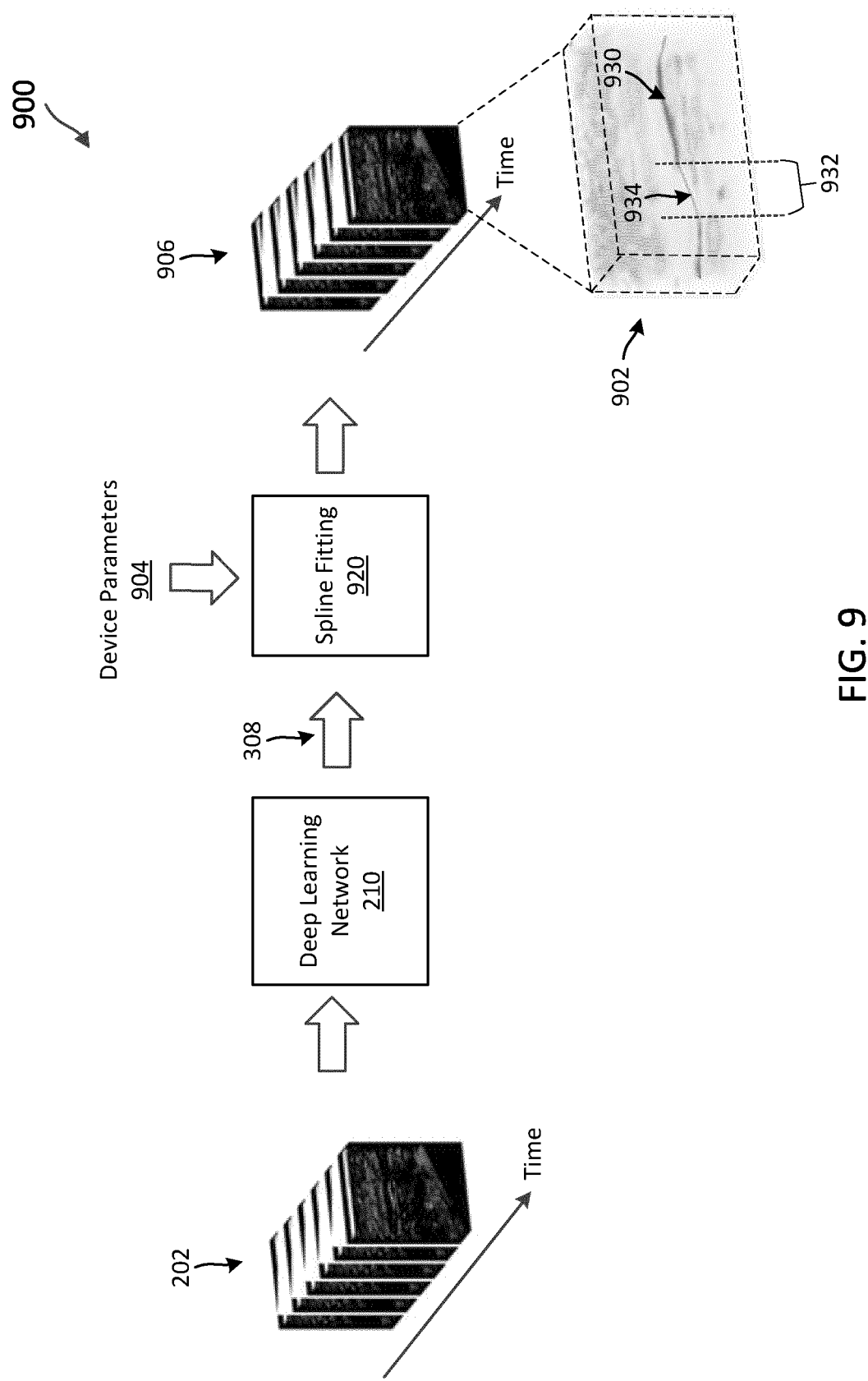
FIG. 9 is a schematic diagram of a deep learning-based image segmentation scheme with spline fitting, according to aspects of the present disclosure.

FIG. 9 is a schematic diagram of a deep learning-based image segmentation scheme 900 with spline fitting, according to aspects of the present disclosure. The scheme 900 is implemented by the system 100. The scheme 900 is substantially similar to the scheme 200. For example, the scheme 900 utilizes a temporally-aware multi-layered deep learning network 210 to provide segmentations of a moving object in ultrasound images. Additionally, the scheme 900 includes a spline fitting component 910 coupled to the output of the deep learning network 210. The spline fitting component 910 can be implemented by the processing component 134 at the system 100.

The spline fitting component 910 is configured to apply a spline fitting function to the confidence maps 308 output by the deep learning network 210. An expanded view of a confidence map 308 for an image frame 202 in the sequence is shown as a heat map 902. As shown, the deep learning network 210 predicted the moving object as shown by the curve 930. However, the curve 930 is discontinuous and includes a gap 932. The spline fitting component 910 is configured to fit a spline 934 to smooth out the discontinuity of the curve 930 at the gap 932. The spline fitting component 910 may perform the spline fitting by taking into account device parameters 904 associated with the moving object under imaging. The device parameters 904 may include the shape of the device, the tip position of the device, and/or other dimensional and/or geometric information of the device. Thus, the use of a spline fitting as postprocessing refinement to the temporal deep learning-based prediction can further improve visualization and/or stability of a moving object under imaging.

Figure 10:
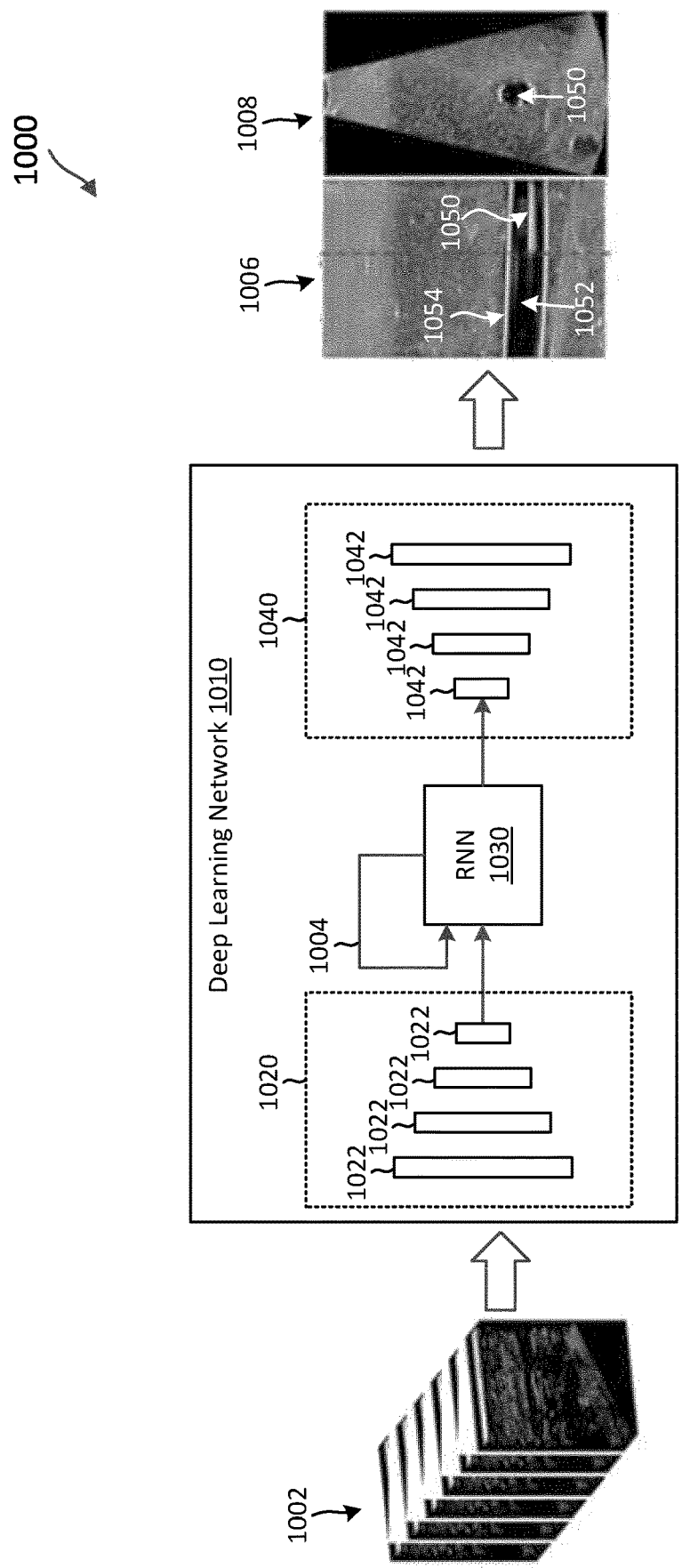
FIG. 10 is a schematic diagram of a deep learning-based imaging guidance scheme, according to aspects of the present disclosure.

FIG. 10 is a schematic diagram of a deep learning-based imaging guidance scheme 1000, according to aspects of the present disclosure. The scheme 1000 implemented by the system 100. The scheme 1000 is substantially similar to the scheme 200. For example, the scheme 1000 utilizes a temporally-aware multi-layered deep learning network 1010 to provide imaging guidance for ultrasound imaging. The deep learning network 1010 may have a substantially similar architecture as the deep learning network 210. For example, the deep learning network 1010 includes a convolutional encoder 1020, a temporally-aware RNN 1030, and a convolutional decoder 2100. The convolutional encoder 1020 includes a plurality of convolutional encoding layers 1022. The convolutional decoder 1040 includes a plurality of convolutional decoding layers 1042. The convolutional encoding layers 1022, the convolutional decoding layers 1042, and the RNN 1030 are substantially similar to the convolutional encoding layers 222, the convolutional decoding layers 242, and the RNN 230, respectively, and may operate at multiple different spatial resolutions (e.g., the spatial resolutions 410, 412, 414, and 416) as shown in the configuration 400. However, the convolutional encoding layers 1022, the convolutional decoding layers 1042, and the RNN 1030 are trained to predict an optimal imaging plane for imaging a target anatomy (e.g., including a particular clinical property of interest). The optimal imaging plane can be a 2D plane, an X-plane (e.g., including a cross-sectional plane and an orthogonal imaging plane), an MPR, or any suitable imaging plane.

For example, a sequence of image frames 1002 is captured across a time period (e.g., from time T0 to time Tn). The image frames 202 may be captured using the system 100. The deep learning network 1010 can be applied to the sequence of image frames 1002 to predict an optimal imaging plane. As an example, the sequence of input image frames 1002 is captured while a medical device 1050 (e.g., the medical device 108) passes through a vessel lumen 1052 with a vessel wall 1054 (e.g., the object 105). The output of the deep learning network 1010 provides an optimal long axis slice 1006 and a short axis slice 1008. Similar to the scheme 200, the each of the image frame 1002 is processed by each of the convolutional encoding layers 1022 and each of the convolutional decoding layers 1042. The RNN 1030 passes a prediction for a current image frame 1002 (captured at time T0) back to the RNN 1030 as a secondary input for a prediction for a next image frame 1002 (captured at time T1) as shown by the arrow 1004.

In a first example, the prediction output by the deep learning network 1010 can be used by the system 100 to automatically steer ultrasound beams to the optimal location. For example, the processing component 116 and/or 134 can be configured to control or steer ultrasound beams generated by the transducer array 112 based on the prediction.

In a second example, the deep learning network 1010 may predict that an optimal imaging plane is an oblique plane. The deep learning network 1010 may provide navigation instructions to a user to maneuver (e.g., rotate and/or translate) the ultrasound probe 110 to align the axis of the probe 110 to the predicted optimal plane. In some examples, the navigation instructions can be displayed on a display similar to the display 132. In some examples, the navigation instructions can be displayed can be displayed using graphical representations (e.g., a rotational symbol or a translational symbol). After the user repositions the probe 110 to the suggested location, the imaging plane may be in a non-oblique plane. Thus, the deep learning network 1010 can transition to provide prediction as described in the first example and may communicate with the processing component 116 and/or 134 to steer beams generated by the transducer array 112.

Figure 11:
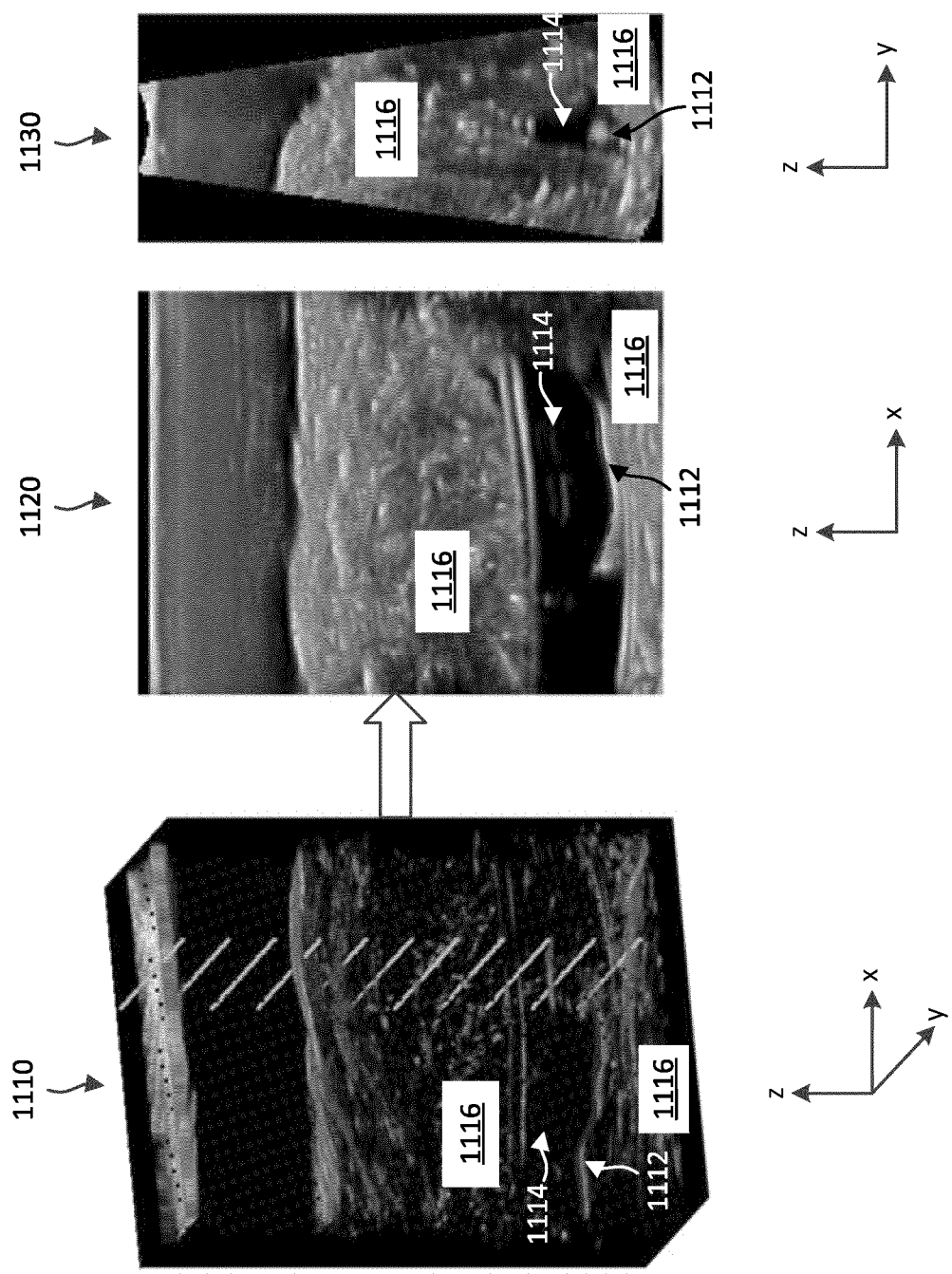
FIG. 11 illustrates ultrasound images obtained from an ultrasound-guided procedure, according to aspects of the present disclosure.

FIG. 11 illustrates ultrasound images 1110, 1120, and 1130 obtained from an ultrasound-guided procedure, according to aspects of the present disclosure. The image 1110 is a 3D image captured using a system similar to the system 100 during a PVD examination. The image 1110 shows a thin guide wire 1112 (e.g., the medical device 108 and/or 1050) traversing through a vessel lumen 1114 surrounded by a vessel wall 1116 (e.g., the object 105). The device 1112 traverses through the vessel along the x-axis. The system may capture a series of 3D images similar to the image 1110 as the device 1112 traverses through the vessel. As described above, the motion of the device 1112 can cause the device 1112 to go in and out of the imaging view. Additionally, the thin geometry of the device 1112 can cause challenges in distinguishing the device 1112 from the anatomy (e.g., the vessel lumen 1114 and/or the vessel walls 1116).

To improve visualization, a temporally-aware deep learning network trained for segmentation and/or imaging guidance can be applied to the series of 3D images (including the image 1110). The prediction results produced by the deep learning network 1010 are used to automatically set MPRs passing through the tip of the device 1112 and aligned with the major axes (e.g., the x-axis and the y-axis) of the device 1112. The images 1120 and 1130 are generated based on the deep learning segmentation. The image 1120 shows a longitudinal MPR (along the z-x plane) constructed from the image 1110 based on prediction results output by the deep learning network. The image 1130 shows a transverse MPR (along the y-z plane) constructed from the image 1110 based on the prediction results. The orthogonal MPR planes (e.g., the images 1120 and 1130) were generated based on the predicted segmentation. In this case, the images 1120 and 1130 correspond to the longitudinal and sagittal planes that pass through the tip of the segmented device 1112, respectively, but other MPR planes can be generated as well using similar mechanisms.

In some cases, the device 1112 can be located in close proximity to the anatomy (e.g., the vessel wall) and can be equally reflective as the anatomy. Thus, a clinician may have difficulty in visualizing the device 1112 from the captured images. To further improve visualization, the image 1120 and 1130 can be color coded. For example, anatomical structures can be shown in a gray-scale and the device 1112 can be shown in red or any other suitable color.

Figure 12:
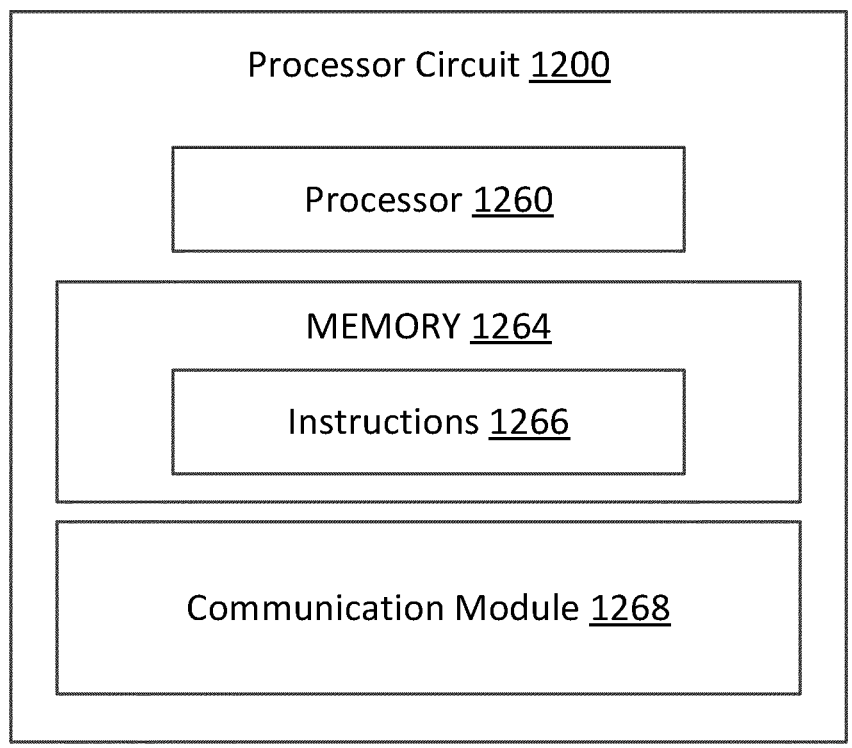
FIG. 12 is a schematic diagram of a processor circuit, according to embodiments of the present disclosure.

FIG. 12 is a schematic diagram of a processor circuit 1200, according to embodiments of the present disclosure. The processor circuit 1200 may be implemented in the probe 110 and/or the host 130 of FIG. 1. As shown, the processor circuit 1200 may include a processor 1260, a memory 1264, and a communication module 1268. These elements may be in direct or indirect communication with each other, for example via one or more buses.

The processor 1260 may include a CPU, a DSP, an application-specific integrated circuit (ASIC), a controller, an FPGA, another hardware device, a firmware device, or any combination thereof configured to perform the operations described herein, for example, aspects of FIGS. 1-11 and 13-15. The processor 1260 may also be implemented as a combination of computing devices, e.g., a combination of a DSP and a microprocessor, a plurality of microprocessors, one or more microprocessors in conjunction with a DSP core, or any other such configuration.

The memory 1264 may include a cache memory (e.g., a cache memory of the processor 1260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1264 includes a non-transitory computer-readable medium. The memory 1264 may store instructions 1266. The instructions 1266 may include instructions that, when executed by the processor 1260, cause the processor 1260 to perform the operations described herein, for example, aspects of FIGS. 1-11 and 13-15 and with reference to the probe 110 and/or the host 130 (FIG. 1). Instructions 1266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 1268 can include any electronic circuitry and/or logic circuitry to facilitate direct or indirect communication of data between the processor circuit 1200, the probe 110, and/or the display 132. In that regard, the communication module 1268 can be an input/output (I/O) device. In some instances, the communication module 1268 facilitates direct or indirect communication between various elements of the processor circuit 1200 and/or the probe 110 (FIG. 1) and/or the host 130 (FIG. 1)

Figure 13:
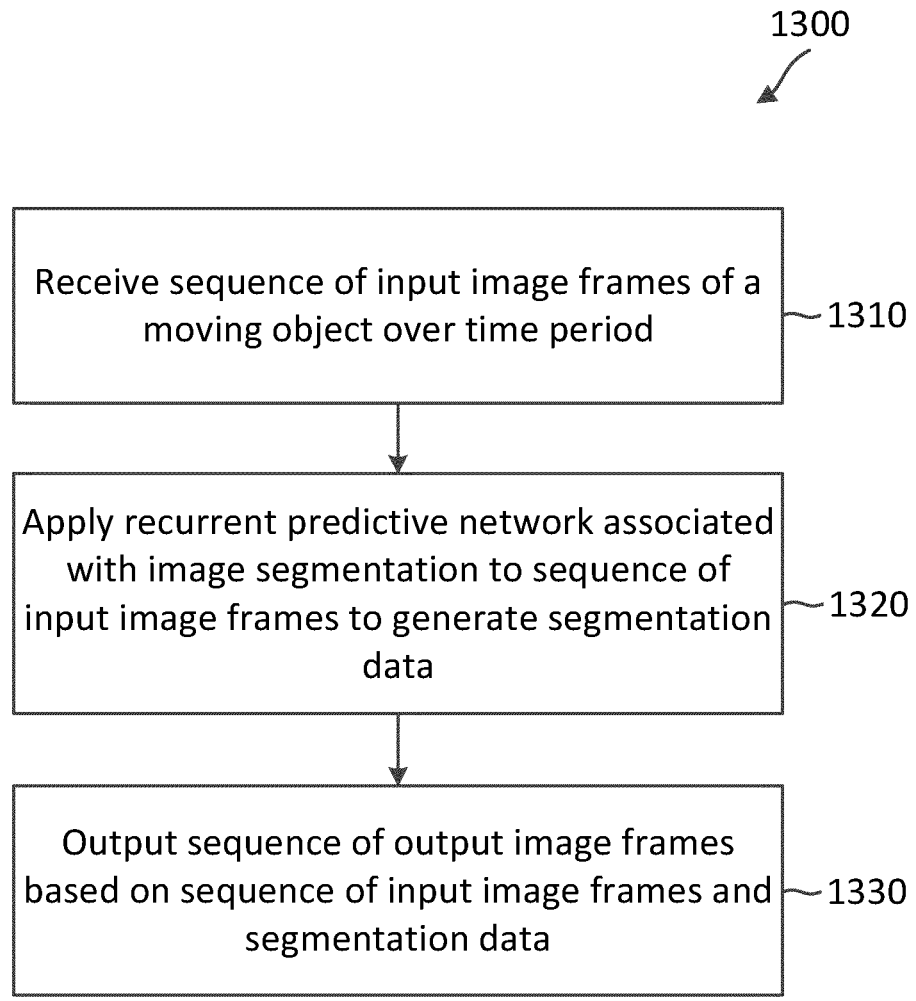
FIG. 13 is a flow diagram of a deep learning-based ultrasound imaging method, according to aspects of the present disclosure.

FIG. 13 is a flow diagram of a deep learning-based ultrasound imaging method 1300, according to aspects of the present disclosure. The method 1300 is implemented by the system 100, for example, by a processor circuit such as the processor circuit 1200, and/or other suitable component such as the probe 110, the processing component 114, the host 130, and/or the processing component 134. In some examples, the system 100 can include computer-readable medium having program code recorded thereon, the program code comprising code for causing the system 100 to execute the steps of the method 1300. The method 1300 may employ similar mechanisms as in the schemes 200, 900, and/or 1000 described with respect to FIGS. 2, 9, 10, respectively, the configurations 300 and/or 400 described with respect to FIGS. 3 and 4, respectively, and/or the scenarios 500, 600, 700, and/or 800 described with respect to FIGS. 5, 6, 7, and/or 8, respectively. As illustrated, the method 1300 includes a number of enumerated steps, but embodiments of the method 1300 may include additional steps before, after, and in between the enumerated steps. In some embodiments, one or more of the enumerated steps may be omitted or performed in a different order.

At step 1310, the method 1300 includes receiving, by a processor circuit (e.g., the processing component 116 and/or 134 and/or the processor circuit 1200) from an ultrasound imaging device (e.g., the probe 110), a sequence of input image frames (e.g., the image frames 202) of a moving object over a time period (e.g., spanning time T0, T1, T2 . . . , Tn). The moving object includes at least one of an anatomy of a patient or a medical device traversing through the patient's anatomy and a portion of the moving object is at least partially invisible in a first input image frame of the sequence of input image frames. The first input image frame may be any image frame in the sequence of input images frames. The anatomy may be similar to the object 105 and may include the patient's heart, lung, vessels (e.g., the vessel lumens 504, 604, 705, and/or 804 and the vessel walls 502, 602, 702, and/or 802), nerve fibers, and/or any suitable anatomical structure of the patient. The medical device is similar to the medical device 108 and/or the guide wires 510, 610, 710, and/or 810.

At step 1320, the method 1300 includes applying, by the processor circuit, a recurrent predictive network (e.g., the deep learning network 210) associated with image segmentation to the sequence of input image frames to generate segmentation data.

At step 1330, the method includes outputting, to a display (e.g., the display 132) in communication with the processor circuit, a sequence of output image frames (e.g., the image frames 206 and/or 906) frames based on the segmentation data. The portion of the moving object is fully visible in a first output image frame of the sequence of output image frames, where the first output image frame and the first input image frame associated with a same time instant within the time period.

In some examples, the portion of the moving object may be within an occluded region (e.g., the occluded region 520), for example, as shown in the scenario 500 described above with respect to FIG. 5. In some examples, the portion of the moving object may be lie against an anatomical structure (e.g., the vessel walls 605, 602, 702, and/or 802) of the patient, for example, as shown in the scenario 600 described above with respect to FIG. 6. In some examples, the portion of the moving object may be captured while acoustic coupling is low or lost, for example, as shown in the scenario 700 described above with respect to FIG. 7. In some examples, the portion of the moving object may be out-of-plane while the first input image frame is captured, for example, as shown in the scenario 800 described above with respect to FIG. 8.

In an embodiment, the applying the recurrent predictive network includes generating previous segmentation data based on a previous input image frame of the sequence of input image frames, where the previous input image frame is received before the first input image frame, and generating first segmentation data based on the first input image frame and previous segmentation data. The previous input image frame can be any image frame in the sequenced received before the first input image frame or an image frame immediately before the first input image frame in the sequence. For example, the first input image frame corresponds to the input image frame $202_{T1}$ received at a current time T1, the first segmentation data corresponds to the output $306_{T1}$, the previous input image frame corresponds to the input image frame $202_{T0}$ received at a previous time T0, and the previous segmentation data corresponds to the output $306_{T0}$ as shown in the configuration 300 described with respect to FIG. 3.

In an embodiment, the generating the previous segmentation data includes applying a convolutional encoder (e.g., the convolutional encoders 220) and a recurrent neural network (e.g., the RNN 230) to the previous input image frame. The generating the first segmentation data includes applying the convolutional encoder to the first input image frame to generate encoded data and applying the recurrent neural network to the encoded data and the previous segmentation data. The applying the recurrent predictive network further includes applying a convolutional decoder (e.g., the convolutional decoder 240) to the first segmentation data and the previous segmentation data. In an embodiment, the convolutional encoder, the recurrent neural network, and the convolutional decoder operate at multiple spatial resolutions (e.g., the spatial resolutions 410, 412, 414, and 416).

In an embodiment, the moving object includes the medical device traversing through the patient's anatomy. In such an embodiment, the convolutional encoder, the recurrent neural network, and the convolutional decoder are trained to identify the medical device from the patient's anatomy and predict a motion associated with the medical device traversing through the patient's anatomy.

In an embodiment, the moving object includes the patient's anatomy with at least one of a cardiac motion, a breathing motion, or an arterial pulse. In such an embodiment, the convolutional encoder, the recurrent network, and the convolutional decoder are trained to identify a moving portion of the patient's anatomy from a static portion of the patient's anatomy and predict a motion associated with the moving portion.

In an embodiment, the moving object includes the medical device traversing through the patient's anatomy and the system includes the medical device. In an embodiment, the medical device comprises at least one of a needle, a guidewire, a catheter, a guided catheter, a therapy device, or an interventional device.

In an embodiment, the input image frames include 3D image frames and the recurrent predictive network is trained for 4D image segmentation based on temporal information. In an embodiment, the sequence of input image frames includes 2D image frames and the recurrent predictive network is trained for 3D image segmentation based on temporal information.

In an embodiment, the method 1300 further includes applying spline fitting (e.g., the spline fitting component 920 to the sequence of input image frames based on the segmentation data. The spline fitting may utilize spatial information and temporal information in the sequence of input image frames and predictions by the recurrent predictive network.

Figure 14:
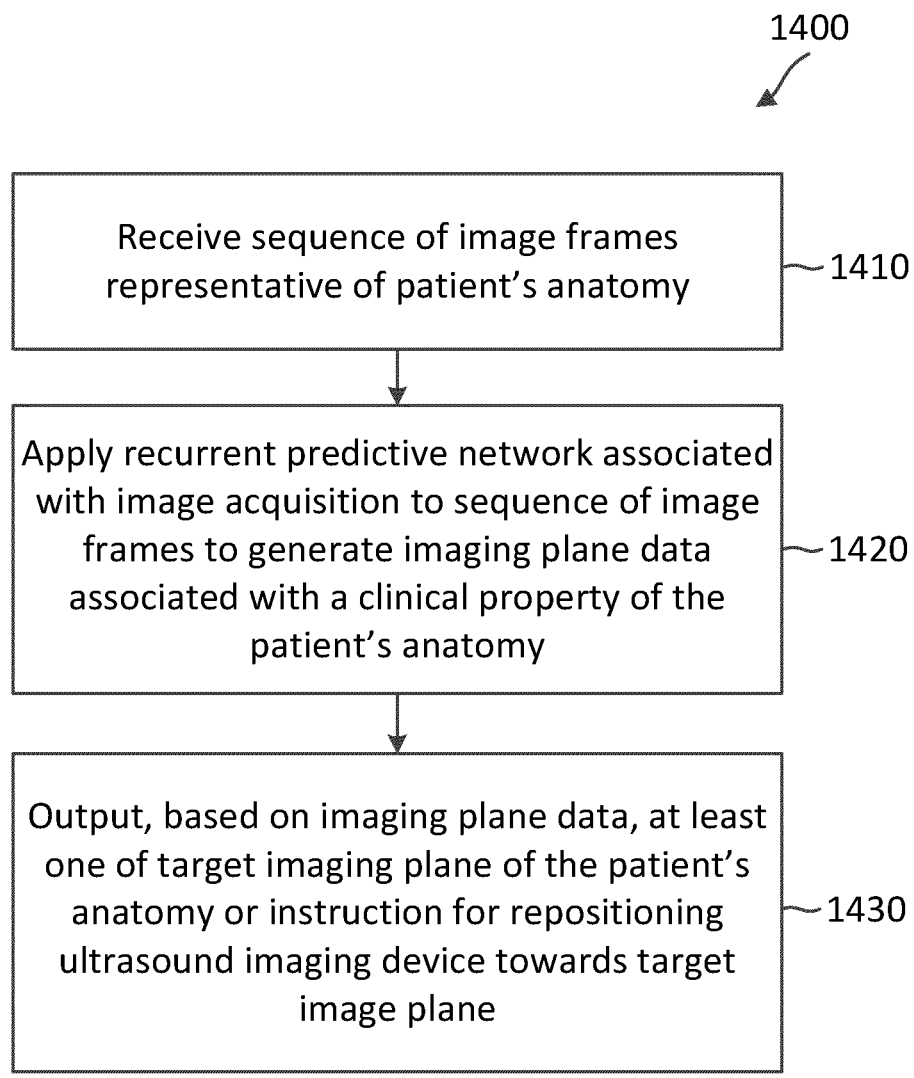
FIG. 14 is a flow diagram of a deep learning-based ultrasound imaging method, according to aspects of the present disclosure.

FIG. 14 is a flow diagram of a deep learning-based ultrasound imaging method, according to aspects of the present disclosure. The method 1400 is implemented by the system 100, for example, by a processor circuit such as the processor circuit 1200, and/or other suitable component such as the probe 110, the processing component 114, the host 130, and/or the processing component 134. In some examples, the system 100 can include computer-readable medium having program code recorded thereon, the program code comprising code for causing the system 100 to execute the steps of the method 1400. The method 1400 may employ similar mechanisms as in the schemes 1000 described with respect to FIG. 10, the configurations 300 and 400 described with respect to FIGS. 3 and 4, respectively. As illustrated, the method 1400 includes a number of enumerated steps, but embodiments of the method 1400 may include additional steps before, after, and in between the enumerated steps. In some embodiments, one or more of the enumerated steps may be omitted or performed in a different order.

At step 1410, the method 1400 includes receiving, by a processor circuit (e.g., the processing component 116 and/or 134 and/or the processor circuit 1200) from an ultrasound imaging device (e.g., the probe 110), a sequence of image frames (e.g., the image frames 1002 and/or 1110) representative of an anatomy of a patient over a time period (e.g., spanning time T0, T1, T2, . . . , Tn). The anatomy may be similar to the object 105 and may include a heart, lungs, and/or any anatomical structure of the patient.

At step 1420, the method 1400 includes applying a recurrent predictive network (e.g., the deep learning network 1010) associated with image acquisition to the sequence of image frames to generate imaging plane data associated with a clinical property of the patient's anatomy. The clinical property may be associated with a heart condition, a lung condition, and/or any other clinical condition.

At step 1430, the method 1400 includes outputting, to a display (e.g., the display 132) in communication with the processor circuit based on the imaging plane data, at least one of a target imaging plane (e.g., a cross-sectional plane, a longitudinal plane, or an MPR plane) of the patient's anatomy or an instruction for repositioning the ultrasound imaging device towards the target imaging plane.

In an embodiment, the applying the recurrent predictive network includes generating first imaging plane data based on a first image frame of the sequence of image and generating second imaging plane data based on a second image frame of the sequence of image frames and the first imaging plane data, the second image frame being received after the first image frame. For example, the first image frame corresponds to the input image frame 1002 received at a previous time T0, the first imaging plane data corresponds to the output of the RNN 1030 at time T0, the second image frame corresponds to the input image frame 1002$_{T1}$ received at a current time T1, and the second imaging plane data correspond to output of the RNN 1030 at time T1, as shown in the scheme 1000 described with respect to FIG. 10.

In an embodiment, the generating the first imaging plane data includes applying a convolutional encoder (e.g., the convolutional encoders 1020) and a recurrent neural network (e.g., the RNN 1030) to the first image frame. The generating the second imaging plane data includes applying the convolutional encoder to the second image frame to generate encoded data and applying the recurrent neural network to the encoded data and the first imaging plane data. The applying the recurrent predictive network further includes applying a convolutional decoder (e.g., the convolutional decoder 1040) to the first imaging plane data and the second imaging plane data. In an embodiment, the convolutional encoder, the recurrent neural network, and the convolutional decoder operate at multiple spatial resolutions (e.g., the spatial resolutions 410, 412, 414, and 416). In an embodiment, the convolutional encoder, the recurrent network, and the convolutional decoder are trained to predict the target imaging plane for imaging the clinical property of the patient's anatomy.

In an embodiment, the input image frames include 3D image frames and the recurrent predictive network is trained for 3D image acquisition based on temporal information. In an embodiment, the sequence of input image frames includes 2D image frames and the recurrent predictive network is trained for 2D image acquisition based on temporal information.

In an embodiment, the method 1400 outputs the target imaging plane including at least one of a cross-sectional image slice (e.g., the image slice 1006 and/or 1120), an orthogonal image slice (e.g., the image slice 1008 and/or 1130), or a multiplanar MPR image slice of the patient's anatomy including the clinical property.

In an embodiment, the method 1400 includes generating an ultrasound beam steering control signal based on the imaging plane data and outputting, to the ultrasound imaging device, the ultrasound beam steering control signal. For example, the ultrasound beam steering control signal may steer ultrasound beams generated by a transducer array (e.g., the transducer array 112) of the ultrasound imaging device.

In an embodiment, the processor circuit outputs the instruction including at least one of a rotation or a translation of the ultrasound imaging device. The instruction can provide a user with guidance in maneuvering the ultrasound imaging device to an optimal imaging location (e.g., the target imaging plane) for obtaining a target image view of the patient's anatomy.

Aspects of the present disclosure can provide several benefits. For example, the use of temporal continuity information in the deep learning network (e.g., the deep learning networks 210 and 1010) allows the deep learning network to learn and predict based on a series of observations in time rather than over a single point in time. The temporal continuity information provides additional dimensionality information that can improve segmentations of elongate flexibly thinly-shaped moving objects that may be otherwise difficult for segmentations. Accordingly, the disclosed embodiments can provide stable view of motions of a moving object under 2D and/or 3D imaging. The use of spline fitting as a refinement to the deep learning network output can further provide a smooth transition of motions associated with the moving object under imaging. The use of temporal continuity information can also provide automatic view-finding, for example, including beam steering controls and/or imaging guidance instructions, in reaching a target imaging view.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
    a processor circuit in communication with an ultrasound imaging device, the processor circuit configured to:
        receive, from the ultrasound imaging device, a temporal sequence of input image frames of a moving object over a time period, wherein the moving object comprises at least one of an anatomy of a patient or a medical device traversing through the patient's anatomy, and wherein a portion of the moving object is at least partially invisible in a first input image frame of the sequence of input image frames;
        apply a recurrent predictive network associated with image segmentation to the sequence of input image frames to generate segmentation data, wherein the recurrent predictive network is adapted to predict motion and/or positions of the moving object based on temporal information carried in the sequence of image frames, and wherein the recurrent predictive network comprises a deep learning network adapted to pass a prediction for a current image frame as an input for a prediction of a next image frame; and
        output, to a display in communication with the processor circuit, a sequence of output image frames based on the segmentation data, wherein the portion of the moving object is fully visible in a first output image frame of the sequence of output image frames, the first output image frame and the first input image frame associated with a same time instant within the time period.

2. The system of claim 1, wherein the processor circuit configured to apply the recurrent predictive network is further configured to:
    generate previous segmentation data based on a previous input image frame of the sequence of input image frames, the previous input image frame being received before the first input image frame; and
    generate first segmentation data based on the first input image frame and the previous segmentation data.

3. The system of claim 2, wherein:
    the processor circuit configured to generate the previous segmentation data is configured to:
        apply a convolutional encoder and a recurrent neural network to the previous input image frame;
    the processor circuit configured to generate the first segmentation data is configured to:
        apply the convolutional encoder to the first input image frame to generate encoded data; and
        apply the recurrent neural network to the encoded data and the previous segmentation data; and
    the processor circuit configured to apply the recurrent predictive network is further configured to:
        apply a convolutional decoder to the first segmentation data and the previous segmentation data.

4. The system of claim 3, wherein the convolutional encoder, the recurrent neural network, and the convolutional decoder operate at multiple spatial resolutions.

5. The system of claim 3, wherein the moving object includes the medical device traversing through the patient's anatomy, and wherein the convolutional encoder, the recurrent neural network, and the convolutional decoder are trained to identify the medical device from the patient's anatomy and predict a motion associated with the medical device traversing through the patient's anatomy.

6. The system of claim 3, wherein the moving object includes the patient's anatomy with at least one of a cardiac motion, a breathing motion, or an arterial pulse, and wherein the convolutional encoder, the recurrent neural network, and the convolutional decoder are trained to identify a moving portion of the patient's anatomy from a static portion of the patient's anatomy and predict a motion associated with the moving portion.

7. The system of claim 1, wherein the moving object includes the medical device traversing through the patient's anatomy, and wherein the system comprises the medical device.

8. The system of claim 7, wherein the medical device comprises at least one of a needle, a guidewire, a catheter, a guided catheter, a therapy device, or an interventional device.

9. The system of claim 1, wherein the input image frames include at least one of two-dimensional image frames or three-dimensional image frames.

10. The system of claim 1, wherein the processor circuit is further configured to:
    apply spline fitting to the sequence of input image frames based on the segmentation data.

11. The system of claim 1, further comprising the ultrasound imaging device, and wherein the ultrasound imaging device comprises an ultrasound transducer array configured to obtain the sequence of input image frames.

12. A method of processing ultrasound images, said method comprising the steps:

receiving, from an ultrasound imaging device, a temporal sequence of image frames representative of an anatomy of a patient over a time period;

applying a recurrent predictive network associated with image acquisition to the sequence of image frames to generate imaging plane data associated with a clinical property of the patient's anatomy, wherein the recurrent predictive network is adapted to predict motion and/or positions of the anatomy of the patient based on temporal information carried in the sequence of image frames, and wherein the recurrent predictive network comprises a deep learning network adapted to pass a prediction for a current image frame as an input for a prediction of a next image frame; and outputting to a display at least one of a target imaging plane of the patient's anatomy or an instruction for repositioning the ultrasound imaging device towards the target imaging plane.

13. The method as claimed in claim 12, wherein the step of applying a recurrent predictive network comprises the steps:

generating first imaging plane data based on a first image frame of the sequence of image frames; and generating second imaging plane data based on a second image frame of the sequence of image frames and the first imaging plane data, the second image frame being received after the first image frame.

14. The method as claimed in claim 13, wherein the step of generating first imaging plane data comprises:

applying a convolutional encoder and a recurrent neural network to the first image frame, wherein the step of generating the second imaging plane data comprises:

applying the convolutional encoder to the first image frame to generate encoded data; and applying the recurrent neural network to the encoded data and the first imaging plane data; imaging plane data:

and wherein the step of applying the recurrent predictive network comprises:

applying a convolutional decoder to the first imaging plane data and the second imaging plane data.

15. A non-transitory computer-readable storage medium having stored thereon a computer program including instructions for configuring a processor circuit to control an ultrasound imaging device, in which the instructions, when executed by the processor circuit, cause the processor circuit to:

receive, from the ultrasound imaging device, a temporal sequence of image frames representative of an anatomy of a patient over a time period;

apply a recurrent predictive network associated with image acquisition to the sequence of image frames to generate imaging plane data associated with a clinical property of the patient's anatomy, wherein the recurrent predictive network is adapted to predict motion and/or positions of the anatomy of the patient based on temporal information carried in the sequence of image frames, and wherein the recurrent predictive network comprises a deep learning network adapted to pass a prediction for a current image frame as an input for a prediction of a next image frame; and output to a display at least one of a target imaging plane of the patient's anatomy or an instruction for repositioning the ultrasound imaging device towards the target imaging plane.

\* \* \* \* \*